United States Patent [19]
Tarin et al.

[11] Patent Number: 5,879,898
[45] Date of Patent: Mar. 9, 1999

[54] ANTIBODIES SPECIFIC FOR PEPTIDE CORRESPONDING TO CD44 EXON 6, AND USE OF THESE ANTIBODIES FOR DIAGNOSIS OF TUMORS

[75] Inventors: David Tarin, Oxford, United Kingdom; Yasuhiro Matsumura, Tokyo, Japan

[73] Assignee: ISIS Innovation Limited, Oxford, England

[21] Appl. No.: 428,138

[22] PCT Filed: Nov. 22, 1993

[86] PCT No.: PCT/GB93/02394

§ 371 Date: May 17, 1995

§ 102(e) Date: May 17, 1995

[87] PCT Pub. No.: WO94/12631

PCT Pub. Date: Jun. 9, 1994

[30]     Foreign Application Priority Data

Nov. 20, 1992  [DE]  Germany ............................ 9224386
Dec. 16, 1992  [DE]  Germany ............................ 9226165
Jul. 20, 1993  [WO]  WIPO ...................... PCTGB9301520

[51] Int. Cl.⁶ ................. G01N 33/53; G01N 33/541; C07K 16/30; C12N 5/12

[52] U.S. Cl. ................. 435/7.21; 435/7.23; 435/70.21; 435/172.2; 435/330; 530/387.3; 530/387.7; 530/387.9; 530/388.2; 530/388.8; 530/388.85; 530/389.7

[58] Field of Search ................. 530/387.9, 388.8, 530/388.85, 389.7, 388.15, 387.3, 387.7, 388.2; 435/172.2, 240.27, 7.21, 7.23, 70.21, 330, 331; 436/547, 548

[56]     References Cited
PUBLICATIONS

Salami et al. 8ᵗʰ Int'l Congress Immunology, Budaphest Hungary Aug., 1992 Abstract 34 274 W–47/I.
Arch, Science 257;682–685, Jul. 1992.
Riechmann, Nature 332;323–327, 1988.
Screaton, PNAS, 89:12160–12161, Dec. 15, 1992.
Current Protocols in Molecular Biology, Ch. 11, 1990 John Wiley & Sons.
Gunthert, Cell 65:13–24, 1991.
Kozbor, Immunology Today 4: 72–78, 1983.

*Primary Examiner*—Lila Feisee
*Assistant Examiner*—Nancy A. Johnson
*Attorney, Agent, or Firm*—Nixon & Vanderhye

[57]     ABSTRACT

There is marked over-expression of multiple spliced variants of the CD44 gene in tumor compared to counterpart normal tissue. This observation forms the basis of a method of diagnosing neoplasia by analysis of a sample of body tissue or body fluid or waste product. A new exon 6 of 129 bp has been located and sequenced. Antibodies specific to the exon have been prepared and are claimed as new compounds suitable for use in the detection of CD44 proteins and for the in vivo imaging and therapy of tumors.

13 Claims, 7 Drawing Sheets

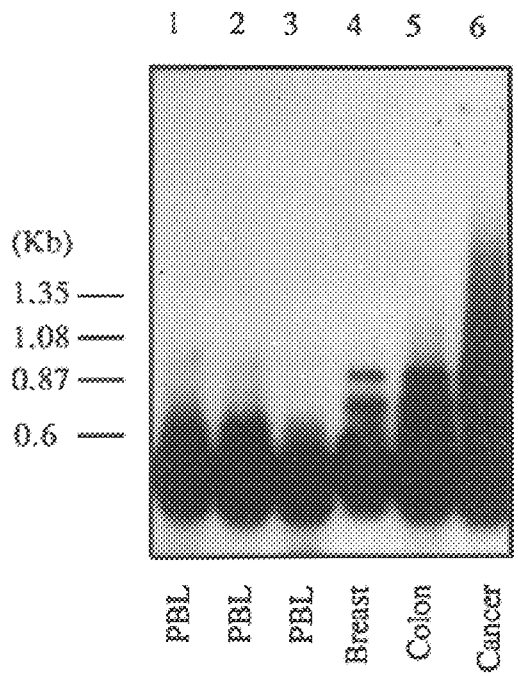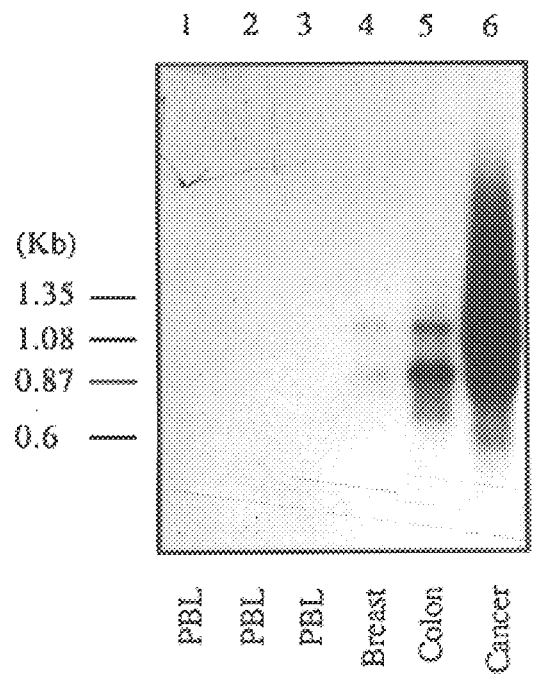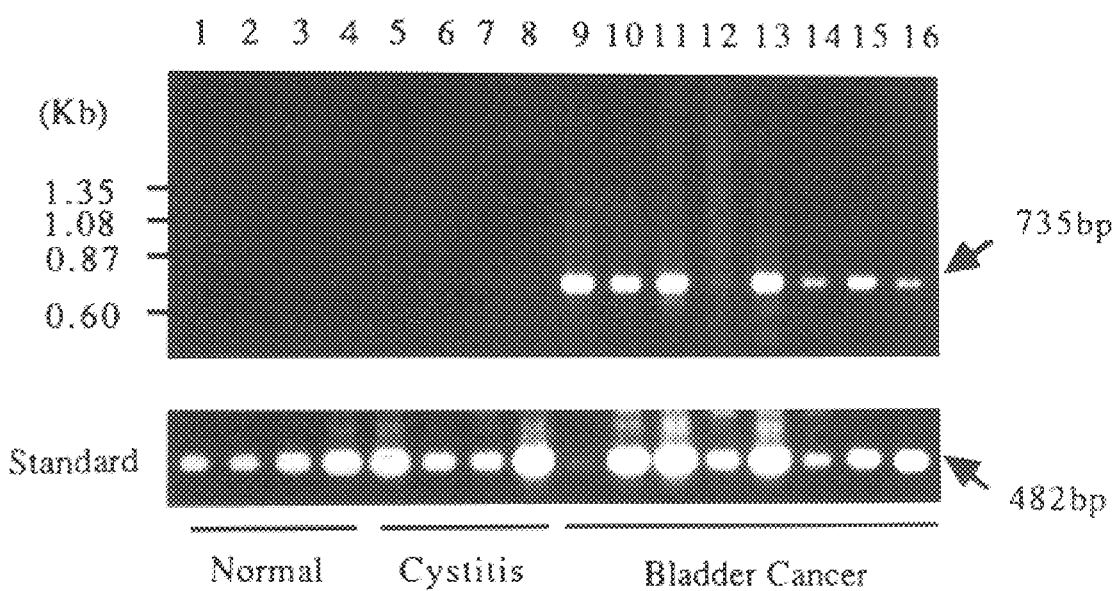

```
         STANDARD │ New Exon (Exon6)
        ─────────◄┼─────────────────►
                  │
         GCTACCACTTTGATGAGCACTAGTGCTACA
             T  L  M  S  T  S  A  T
                      ─  ─  ─

GCAACTGAGACAGCAACCAAGAGGCAAGAA
          A  T  E  T  A  T  K  R  Q  E

ACCTGGGATTGGTTTTCATGGTTGTTTCTA
          T  W  D  W  F  S  W  L  F  L

CCATCAGAGTCAAAGAATCATCTTCACACA
          P  S  E  S  K  N  H  L  H  T
                                     ─

ACAACACAAATGGCTGGTACG      (SEQ ID No:1)
          T  T  Q  M  A │
          ─  ─          │ Exon 7
                        ┼────────►
```

FIG. 7

Fig. 9  DNA sequence of HIV2(gp32)-CD44 exon 6 fusiongene

```
ATGAGAGGAT CGCATCACCA TCACCATCAC ACGGATCCAG AATTCCAACA   50
GCAACAGCAG TTGTTGGACG TTGTTAAACG TCAACAGGAA CTGTTGCGTC  100
TGACCGTTTG GGGAACCAAG AACCTTCAGG CTAGAGTTAC CGCTATCGAA  150
AAATACCTTC AAGACCAGGC TCGTTTGAAC TCCTGGGGTT GCGCTTTTAG  200
ACAGGTTTGT CATACCACGG TACCGTGGGT TAACGACTCT CTGGCTCCAG  250
ACTGGGACAA CATGACCTGG CAGGAATGGG AAAAGCAAGT TCGTTACTTG  300
GAAGCTAACA TCTCCAAATC TCTGGAACAG GCTCAAATCC AGCAAGAAAA  350
AAACATGTAC GAACTGCAGA AGTTGAACTC TTGGGATATC AGATCCCCGG  400
CTACCACTTT GATGAGCACT AGTGCTACAG CAACTGAGAC AGCAACCAAG  450
AGGCAAGAAA CCTGGGATTG GTTTTCATGG TTGTTTCTAC CATCAGAGTC  500
AAAGAATCAT CTTCACACAA CAACACAAAT GGCTCCGGCC ACCACTTTGA  550
TGAGCACTAG TGCTACAGCA ACTGAGACAG CAACCAAGAG GCAAGAAACC  600
TGGGATTGGT TTTCATGGTT GTTTCTACCA TCAGAGTCAA AGAATCATCT  650
TCACACAACA ACACAAATGG CT                                672
```

Fig. 10  Protein sequence of HIV2(gp32)-CD44 exon 6 fusionantigen

```
MRGSHHHHHH TDPEFQQQQQ LLDVVKRQQE LLRLTVWGTK NLQARVTAIE   50
  (His)             HIV2 (gp32) (117 aa)
KYLQDQARLN SWGCAPRQVC HTTVPWVNDS LAPDWDNMTW QEWEKQVRYL  100
EANISKSLEQ AQ1QQEKNMY ELQKLNSWDI RSPATTLMST SATATETATK  150
                            Exon 5 (3 aa) Exon 6 (43 aa)
RQETWDWFSW LFLPSESKNH LHTTTQMAPA TTLMSTSATA TETATKRQET  200
                     Exon 5 (3 aa) Exon 6 (43 aa)
WDWFSWLFLP SESKNHLHTT TQMA                             224
``` aa = "amino acid"

ns. Further mAbs to this antigen later became available and Stamenkovic et al. (1989) used one of them to clone a cDNA sequence coding for the standard form of the molecule from an expression library in COS cells. They additionally found, by Northern blotting, that this gene was expressed not only by lymphoid cells, but also by a variety of carcinoma cell lines and a representative sample of solid carcinomas, amongst which two colonic carcinomas appeared to express more than normal colonic epithelium.

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 141 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 7..135

( x i ) SEQUENCE DESCRIPTION: SEQ ID NO: 1:

-continued

```
GCTACC  ACT  TTG  ATG  AGC  ACT  AGT  GCT  ACA  GCA  ACT  GAG  ACA  GCA  ACC              48
        Thr  Leu  Met  Ser  Thr  Ser  Ala  Thr  Ala  Thr  Glu  Thr  Ala  Thr
         1                   5                        10

AAG  AGG  CAA  GAA  ACC  TGG  GAT  TGG  TTT  TCA  TGG  TTG  TTT  CTA  CCA  TCA              96
Lys  Arg  Gln  Glu  Thr  Trp  Asp  Trp  Phe  Ser  Trp  Leu  Phe  Leu  Pro  Ser
 15                  20                        25                        30

GAG  TCA  AAG  AAT  CAT  CTT  CAC  ACA  ACA  ACA  CAA  ATG  GCT  GGTACG                   141
Glu  Ser  Lys  Asn  His  Leu  His  Thr  Thr  Thr  Gln  Met  Ala
                     35                        40
```

( 2 ) INFORMATION FOR SEQ ID NO: 2:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Thr  Leu  Met  Ser  Thr  Ser  Ala  Thr  Ala  Thr  Glu  Thr  Ala  Thr  Lys  Arg
 1                   5                        10                       15

Gln  Glu  Thr  Trp  Asp  Trp  Phe  Ser  Trp  Leu  Phe  Leu  Pro  Ser  Glu  Ser
               20                        25                       30

Lys  Asn  His  Leu  His  Thr  Thr  Thr  Gln  Met  Ala
               35                   40
```

ANTIBODIES SPECIFIC FOR PEPTIDE CORRESPONDING TO CD44 EXON 6, AND USE OF THESE ANTIBODIES FOR DIAGNOSIS OF TUMORS

BACKGROUND

The present invention is concerned with using expression of the CD44 gene or part of the CD44 gene to investigate neoplasia. Such investigation includes taking a tissue, body fluid or other sample from a patient to perform diagnosis, to give a prognosis or to evaluate therapy that is already being carried out. In particular, the invention provides a simple method for carrying out routine screening for neoplasia using body fluid samples or other samples which can be obtained non-invasively.

The usual way to diagnose a tumour at present is by looking at cells or thin slices of tissue down a microscope, a method which is often very effective but has some important limitations. With a small sample, diagnosis can be very difficult and often a large number of cells will not be available, or it is not desirable or possible to obtain a large sample from the patient. In as many as 50% of cases a reliable diagnosis cannot be given; it may be that there is no positive evidence of carcinoma but also no certainty that the patient is actually free from carcinoma. More invasive investigation is then required to establish a diagnosis.

Judgment of prognosis also relies on the appearance of cells when viewed under a microscope. Generally, the more bizarre-looking the cells in a primary tumour, the more likely they are to metastasise later on but the correlation is by no means absolute. It would clearly be an advantage to be able to predict more accurately whether or not metastasis is likely to occur in order to judge what will be the most effective treatment.

The human CD44 gene codes for a family of variably glycosylated cell surface proteins of different sizes, the numerous functions of which are not yet fully established, but which share epitopes recognised by the CD44 monoclonal antibody (mAb). It is known to consist of a standard portion which is expressed in haemopoietic cells and many other cell types and into which the products of additional exons may be spliced in various combinations to produce different proteins. This is a well recognised mechanism in eukaryotes for producing several often functionally unrelated proteins from the same gene, and is known as alternative splicing.

Two common CD44 isoforms have so far been purified and characterised (Stamenkovic et al. 1989), namely i) a 90 kD form consisting of a central 37 kD core which is heavily glycosylated and ii) a 180 kD form which has 135 extra amino acids inserted into the proximal extra-membrane domain and is even more heavily glycosylated. Immunocytochemical and immuno-precipitation studies have shown that both are widely distributed in many different cells and tissues. The former is known as the haemopoietic or standard form which is present on circulating leukocytes, bone marrow cells and numerous other cell types. The other, known as the epithelial variant, is detectable on several epithelial cell types. Both are believed to function as receptors mediating homotypic and heterotypic adhesive interactions, attaching cells to each other or to adjacent extracellular scaffolding.

Some time ago, some of the CD44 epitopes recognised by the mAb Hermes-3 were identified as constituting the peripheral lymph node receptor enabling circulating lymphocytes to recognise and traffic through peripheral lymph nodes. Further mAbs to this antigen later became available and Stamenkovic et al. (1989) used one of them to clone a cDNA sequence coding for the standard form of the molecule from an expression library in COS cells. They additionally found, by Northern blotting, that this gene was expressed not only by lymphoid cells, but also by a variety of carcinoma cell lines and a representative sample of solid carcinomas, amongst which two colonic carcinomas appeared to express more than normal colonic epithelium.

Birch and colleagues (1991) reported that melanoma cell clones which strongly expressed the 80–90 kD form of the CD44 antigen, recognised by the Hermes-3 antibody, were substantially more metastatic in nude mice than clones which expressed it weakly. Sy et al. (1991) described a moderate increase in metastatic capability of human lymphoma cells in nude mice, after the cells were transfected with the standard CD44 gene, but not after transfection with a construct coding for the epithelial variant. Gunthert et al. (1991) obtained results indicating that a variant form of the lymphocyte homing receptor, recognised by a new antibody raised to the rat CD44 antigen, is required for metastatic behaviour of rat pancreatic adenocarcinoma cells. Using this antibody they cloned a cDNA sequence corresponding to the variant form of CD44 and found that it contained previously unidentified exons. Transfection of a non-metastatic clone from the same cell line with a construct designed to overexpress this cDNA sequence unique to the metastatic counterpart, appeared to induce metastatic behaviour (Gunthert et al, 1991).

In view of these findings it became of interest to know whether other cultured metastatic and non-metastatic human tumour cell lines, of various histogenetic origins, expressed CD44 produces differentially. The expression of genes in cells or tissues can be studied most efficiently and sensitively by making cDNA from cellular messenger RNA and amplifying regions of interest with the polymerase chain reaction, using specific oligonucleotide primers chosen to anneal preferentially to portions of the cDNA corresponding to the gene products. However, subsequent work by Hofmann et al. (1991) and the present applicants using this approach provided results which showed that CD44 expression did not regularly and reliably correlate with the metastatic capability or even tumour forming ability of these cultured cell lines in nude mice. At about this time, three separate groups (Hofmann et al, 1991, Stamenkovic et al, 1991 and Jackson et al, 1992) published sequence data on further splice variants they had found being expressed by this gene in various human cell lines.

THE INVENTION

The present invention results from a surprising discovery resulting from studies examining the expression of various parts of the CD44 gene in fresh tissue and body fluid samples from patients with tumours of the breast and colon and from their metastases. The results indicate sharp and clear differences in CD44 expression between tissues from i) metastatic (malignant) tumours, ii) non-metastatic locally invasive tumours and benign tumours and iii) normal tissue. The distinction between groups i) and ii) is important for judgment of therapy and that between groups ii) and iii) is important for early diagnosis and screening.

Part of this invention forms the subject of our International patent application PCT/GB93/01520 filed 20 Jul. 1993, which provides in one aspect a method of diagnosis of neoplasia, which method comprises analysing the expression of the CD44 gene in a sample.

In a particular embodiment, that application provides a method of assaying a sample for products of the CD44 gene or part thereof which method comprises making cDNA from messenger RNA (mRNA) in the sample, amplifying portions of the complementary DNA (cDNA) corresponding to the CD44 gene or part thereof and detecting the amplified cDNA, characterised in that the amplified cDNA is used in diagnosis of neoplasia.

The diagnosis of neoplasia may refer to the initial detection of neoplastic tissue or it may be the step of distinguishing between metastatic and non-metastatic tumours. References to the term "diagnosis" as used herein are to be understood accordingly.

The method is particularly applicable to the diagnosis of solid tumours particularly malignant tumours e.g. carcinomas. The sample on which the assay is performed is preferably of body tissue or body fluid; and not of cells cultured in vitro. The sample may be a small piece of tissue or a fine needle aspirate (FNA) of cells from a solid tumour. Alternatively, it may be a sample of blood or urine or another body fluid, a cervical scraping or a non-invasively obtained sample such as sputum, urine or stool.

The cDNA may be detected by use of one or more labelled specific oligonucleotide probes, the probes being chosen so as to be capable of annealing to part of the amplified cDNA sequence. Alternatively, labelled oligonucleotide primers and/or labelled mononucleotides could be used. There are a number of suitable detectable labels which can be employed, including radiolabels.

BRIEF DESCRIPTION OF THE DRAWINGS

Reference is directed to the accompanying drawings, in which:

FIGS. 1A, 1B, 1C, 2A, 2B, 2C, 3, 4, 5A and 5B are autoradiographs showing the results of various experiments reported below, FIG. 8 is a set of autoradiographs showing the results of another experiment.

FIG. 9 is the DNA sequence of HIV2(gp32)-CD44 exon 6 fusiongene.

FIG. 10 is the protein sequence of HIV2(gp32)-CD44 exon 6 fusionantigen.

DETAILED DESCRIPTION OF PREFERRED EMBODIMENTS

Figure 6:
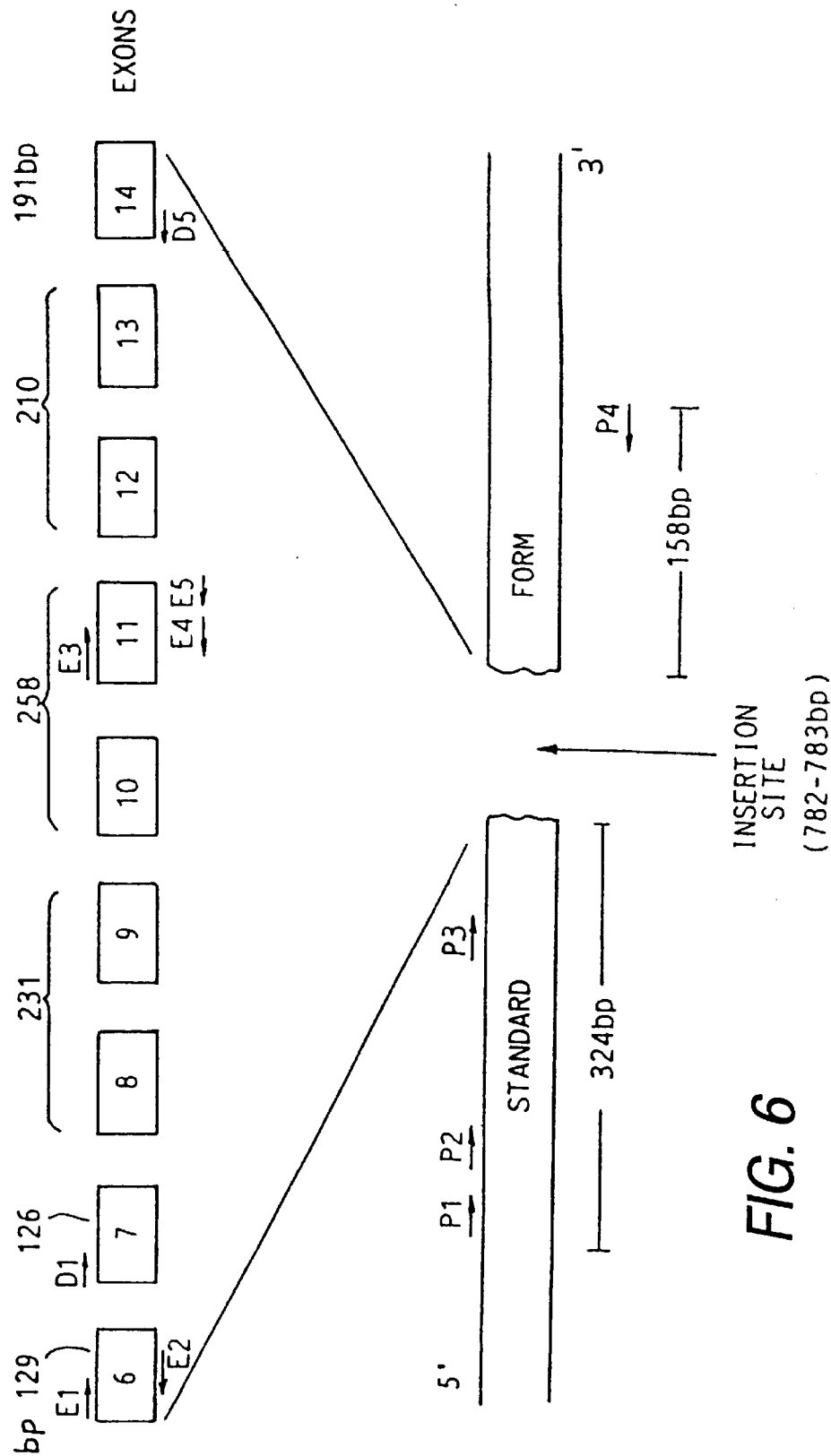
FIG. 6 is a map of the CD44 gene showing exons, probes and primers. The numbering of the exons corresponds to that used by G. R. Screaton et al. 1992), FIG. 7 (SEQ ID NO:1) is the nucleic acid sequence of Exon 6 (shown in FIG. 6), the corresponding amino acid sequence being also shown (SEQ ID NO:2)

FIG. 6 is a map of the CD44 gene showing exons 6 to 14. The basic or standard protein can theoretically be modified by the insertion of transcripts from any, some, or all of these 9 extra exons. Exon 6 was unknown at the priority date of this patent application, and constitutes a further aspect of the invention. Exon 6 is over-expressed in tumours but not in normal tissues, and is located in the vicinity of exons 7 to 9. The sequence of exon 6 is given in FIG. 7. It contains 129 base pairs and is flanked on the 5'-side by the standard CD44 sequence, and on the 3'-side usually by exon 7.

In contrast to Exons 9 to 11, the products of Exon 6 (the newly-sequenced Exon) are only barely detectable in samples of normal tissues. This suggests that Exon 6 will be of particular value in the diagnosis of neoplasia.

In another aspect, that application provides as new compounds, the nucleic acid sequence of Exon 6 as shown in FIG. 7, characteristic fragments thereof, sequences which are degenerated and/or represent allele variations, the homologous nucleic acid sequences, and probes, primers and other reagents capable of hybridising with the sequences or homologues. These compounds and reagents will all be useful in the method described above.

In accordance with the present invention the peptide sequence corresponding to CD44 exon 6 as shown in FIG. 7, its allele variations and secondary modifications thereof and characteristic fragments thereof can be used the generate antibodies useful for the in vitro and in vivo diagnosis. Said antibodies are specific to the peptide corresponding to CD44 exon 6 as shown in FIG. 7, its allele variations and secondary modifications thereof and characteristic fragments thereof i.e. these antibodies bind to this peptide and possess a low cross-reactivity towards other related CD44 proteins and other proteins. Said antibodies may be monoclonal or polyclonal. The antibodies may be generated by using the entire peptide sequence corresponding to CD44 exon 6 as shown in FIG. 7 as an antigen or by using short peptides preferably of a minimum length of six amino acids encoding portions of the peptide sequence corresponding to CD44 exon 6, as antigens. The peptides used as antigens can be produced recombinantely or chemically by methods known in the art. The peptide antigens according to the invention can for example be synthesized according to Merryfield, JACS 85 (1964), 2146. For immunogen synthesis these peptides can be coupled to a carrier molecule for example keyhole limpet hemocyanin (KLH) or bovine serum albumin (BSA). If a biotinylation is required this can for example be carried out according to PNAS U.S.A. 80 (1983), 4045.

For the expression of the peptide corresponding to CD44 exon 6 or its allele variations in a procaryotic host it is prefered to prepare a fusion gene of CD44 exon 6 or its allele variations with a gene which possess a high expression level in this host. For example a part of the gene encoding for the protein gp 32 of HIV 2 is suitable for E. coli. Thereby a fusion protein which possesses as a part the peptide sequence according to Exon 6 or its allele variations is obtained. It is also prefered to increase the number of the peptide epitopes corresponding to CD44 exon 6 in such a fusion protein for example by duplicating the CD44 exon 6 gene in the fusion gene.

Polyclonal antibodies directed against the peptide sequence corresponding to CD44 exon 6, its allele variations and secondary modifications thereof and characteristic fragments are prepared by injection of suitable laboratory animal with an effective amount of a peptide or antigenic component, collecting serum from the animal, and isolating specific antibodies by any of the known immuno absorbent techniques. Although the polyclonal antibodies produced by this method are utilizable in any type of immunoassay, they are generally less favoured because of the potential heterogeneity.

The use of monoclonal antibodies in the in vitro diagnostic test is particularly preferred because large quantities of antibodies all of similar specificity may be produced. The preparation of hybridoma cell lines for monoclonal antibody production is done by fusion of an immortal cell line and the antibody producing lymphocytes. This can be done by techniques which are well known in the art (see for example Harlow, E. and Lane, D., Antibodies: A Laboratory Manual, Cold Spring Harbour Press 1988, Bessler et al. Immunobiol. 170 (1985), 239–244, Jung et al., Angew. Chemie 97 (1985), 883 or Cianfriglia et al., Hybridoma Vol. 2, (1983), 451–457).

The following hybridoma cell lines which are producing monoclonal antibodies directed against the expression product of CD44 exon 6 as shown in FIG. 7 or a fragment thereof e. g. a characteristic epitope were deposited on 16. Nov. 1993 under the Budapest Treaty at the DSM (Deutsche Sammlung von Mikroorganismen und Zellkulturen GmbH, Mascheroder Weg 1b, D-3300 Braunschweig, Federal Republic of Germany:

MAK<CD44>M-1.1.12 DSM ACC2156
MAK<CD44>M-2.42.3 DSM ACC2157
MAK<CD44>M-4.3.16 DSN ACC2158

For MAK<CD44>M-1.1.12 a synthetic peptide corresponding to amino acids 9–23, for MAK<CD44>M-2.42.3 a synthetic peptide corresponding to amino acids 29–43 and for MAK<CD44>M-4.3.16 a synthetic peptide corresponding to amino acids 1–13 of the CD44 exon 6 peptide having the amino acid sequence shown in FIG. 7 was used. The antibody produced by the cell line MAK<CD44>M-1.1.12 shows a specificity to tumor tissue of lung, colon and bladder and for cells of the cell line ZR75-1 (human breast carcinoma—ATCC CRL 1500) as detected by immunohistochemistry. A specific reaction means that a strong reaction is observed with the tumor tissue whereas normal tissue shows only a weak reaction. In the same system the antibody produced by the cell line MAK<CD44>M-4.3.16 shows specificity towards tumor tissue of colon and ZR75-1 cells.

The presence of the CD 44 protein or the peptide sequence according to CD44 exon 6 in a sample can be detected utilizing antibodies prepared as discribed above either monoclonal or polyclonal in virtually any type of immunoassay. A wide range of immunoassay techniques are available as can be seen by reference to Harlow, et al. (Antibodies: A Laboratory Manual, Cold Spring Harbour Press 1988). This of course includes both single-site and two-site, or "sandwich" of the non-competitive types, as well as competitive binding assays. Sandwich assays are among the most useful and commonly used assays. A number of variations of the sandwich assay technique exist, and all are intended to be encompassed by the present invention. Examples for those assays are radio immunoassays, enzyme immunoassays or immunofluorescent assays such as FPIA or electrochemilumineszent assays, immunoassays using direct labels such as dye particles (e.g. gold sol particles), homogeneous immunoassays such as CEDIA or EMIT or turbidimetric and nephelometric methods such as latex particle agglutination assays. It is possible to use two antibodies according to the invention in a sandwich assay. In this case these two antibodies must bind to different epitopes or sites of the peptide sequence according to CD44 exon 6. These antibodies could for example be prepared by using two different synthetic peptides as immunogens corresponding to different characteristic fragments of the peptide corresponding to CD44 exon 6. It is also possible to use only one antibody according to the invention in a sandwich assay. The other antibody could be an antibody to the other peptides corresponding to other CD44 exons or to the standard form of CD44. Such antibodies are known in the art.

It is possible to use for example urine, whole blood, cervical smears, stool, tissue for example biopsies, sputum or cells as sample. In most cases the CD44 protein could be detected in its native form. Preferably the CD44 protein is denatured prior to or during its detection because some of the antibodies according to the invention preferably bind to epitopes which are linear or which are hidden within the CD44 molecule in its native form. As a denaturation method any method known in the art such as treatment with detergent or chaotropic agents is suitable. In some cases the adsorption of the CD44 molecule to a solid phase leads to a partial denaturation which is sufficient for the binding of the antibody.

Although CD44 proteins are expressed on most cell types it was found that with the use of the antibodies according to the invention a differentiation between tumor tissue and normal tissue is possible in most cases. The antibodies therefore could be used in cancer diagnosis. Preferably the antibodies could be used for the diagnosis for cancer of tissue of colon, bladder or lung. For example with the antibody obtainable from the hybridoma cell line MAK<CD44>M-1.1.12 a strong reaction is observed in immunohistochemistry with colon, bladder or lung carcinoma tissue wheras normal tissue of this origin gives only a weak reaction.

It is also possible to utilise the antibodies according to the invention in immune complex analysis for example in a method according to Wong et al., Arch. Surg. 125 (1990), 187–191. Thereby the detection of tumor-associated immune complexes of CD44 protein or characteristic parts thereof and autoantibodies is possible.

The peptide antigens according to the invention can also be used as a standard compound in immunological tests for the quantitative determination of CD 44. The invention therefore in addition concerns the use of the peptide antigens according to the invention as a standard in an immunological test for the determination of CD 44. In certain cases, for example in agglutination tests, it may be advantageous to bind several peptides according to the invention with the same or different sequences to a carrier molecule. The peptides according to the invention can also be used as a binding partner for the antibody according to the invention in a competitive immunoassay. In this case the peptides are labeled or bound to a solid phase directly or indirectly via two specific binding partners such as (strept)avidin/biotin by methods known in the art.

Another aspect of the invention is a test kit containing at least one antibody which is directed against the peptide corresponding to CD44 exon 6 having the amino acid sequence as shown in FIG. 7, its allele variations or secondary modifications thereof or characteristic fragments thereof among the other compounds which are necessary for the immunoassay such as buffers, detergents, stabilizers, solid phases etc. If required the peptide antigens according to the invention as a standard could also be included.

In still another important aspect, this invention provides a means for therapy and in vivo imaging of tumours. Agents useful for this can be manufactured according to the state of the art. The data obtained from studies examining the expression of various parts of the CD44 gene in samples from patients with malignant diseases surprisingly show a significant overexpression of exon 6 of the variable part of CD44. The relative abundance of CD44 splice variants containing exon 6 in malignant tumours as compared to normal tissue and the increased amount of CD44 proteins containing the peptide sequence encoded by exon 6 on the surface of tumour cells as compared to normal tissue opens the possibility to use the exon 6 encoded peptide sequence as a tumour specific antigen for therapy, diagnosis both in vivo and in vitro, and in vivo imaging.

Preferably, monoclonal antibodies (Kohler and Milstein (1975), Nature 156, 495–497) or their derivatives will be used for diagnostic and therapeutic purposes. In this invention, monoclonal antibodies to epitopes encoded by exon 6 of CD44 are provided. Furthermore, data are presented, showing selective binding of these antibodies to tumour cells.

The antibodies according to the invention recognize the peptide corresponding to CD44 exon 6 having the amino acid sequence shown in FIG. 7, its allel variations and phosphorylation and glycosylation products and characteristic fragments thereof. Such antibodies are specific to the peptide corresponding to CD44 exon 6 also in the presence of other peptides which correspond to other CD44 exons. For therapeutic purposes this specificity is defined to the effect that the antibody according to the invention binds only to a little extent to proteins other than the protein encoded by exon 6. This unspecific binding must be so little as to ensure that no considerable damage will be caused to healthy cells when the antibodies according to the invention are used for tumour therapy or in vivo diagnosis.

The antibodies can be used as whole antibodies, fragments thereof (e.g. Fv, (Fv)$_2$, Fab, Fab', F(ab)$_2$, chimeric, humanized or human antibodies as long as they are binding the exon 6 protein in a suitable manner. Short-chain antibody fragments containing only the CDR regions or parts thereof conferring the specific binding to the exon 6 peptide are also suitable, especially if the antibody is a labelled one.

Here the antibodies can be used as a whole for therapy of malignant diseases (Hale et al., Lancet 2 (1988) 1394–1399; Cobbold et al., Prog. Clin. Biol. Res. (1990) 333, 139–151). In another approach, the antibody or part of it is conjugated or translationally fused to a toxin molecule (immunotoxin), thus effecting specific killing of tumour cells (Brinkmann et al. 1991, Proc. Natl. Acad. Sci. USA 88, 8616–8620; Pastan et al. (1991), Cancer Res. 51, 3781–3787; FitzGerald and Pastan (1989), J. Natl. Cancer Inst. 81, 1455–1461). In another preferred embodiment of the invention, bispecific antibodies are used for tumour therapy (Bonino et al. (1992), BFE 9, 719–723), which may be constructed by in vitro reassociation of polypeptide chains, by hybrid hybridoma generation or by construction of diabodies (Holliger et al. (1993), Proc. Natl. Acad. Sci. USA 90, 6444–6448; Holliger and Winter (1993), Current Opin. Biotechnol. 4, 446–449).

In addition, antibodies coupled to radioactive or fluorescent substances are preferred for detection and treatment of tumours, including carcinomas of the respiratory, gastrointestinal and urogenital system as well as ocular and skin cancers (Profio (1988), Proc. Soc. Photoopt. Instr. Eng. 907, 150–156; Jiang et al. (1991), J. Natl. Cancer Inst. 83, 1218–1225).

For prevention of an immune response, it is preferred to use antibodies which resemble as closely as possible antibodies of human origin (Glassy and Dillman (1988), Mol. Biother. 1, 7–13). Such antibodies are, for example, chimeric or humanized (CDR-grafted) antibodies. Such antibodies usually are manufactured from a rodent monoclonal antibody (see e.g. for review: Morrison (1992), Annu. Rev. Immunol. 10, 239–265; Winter and Milstein (1991), Nature 349, 293–299). In a specifically preferred embodiment of the invention, tumour specific human antibodies (Borrebaeck et al. (1988), Proc. Natl. Acad. Sci. USA 85, 3995–3999; Borrebaeck (1988), Immunol. Today 9, 355–359) are used for therapeutic purposes. In addition, it is specifically preferred to prepare human Mabs via phage display libraries, as is described, for example, by Griffith et al., EMBO J. 12 (1993) 725–734.

It is specifically preferred to use, for therapeutic purposes, antibodies which impart effector functions (ADCC, CDC) (Bruggemann et al., J. Exp. Med. 166 (1987) 1357–1361). Particularly preferably, a human isotype IgG 1 antibody is used.

With regard to immunotoxins, it is preferred to couple the antibody according to the invention to a toxin, such as, for example, Pseudomonas exotoxin, Diphtheria toxin or other toxins (FitzGerald and Pastan (1989)). It is also preferred to couple the antibodies to chemotherapeutics, such as, for instance doxorubicin, or to radioactively labelled substances which have a cytotoxic effect.

Conjugates of the antibodies according to the invention, in particular of human antibodies, for in vivo imaging, using, for instance, radioactive or fluorescent substances, are also preferred.

The therapeutic compounds of this invention may be administered parenterally, such as intravascularly, intraperitoneally, subcutaneously, intramuscularily, using forms known in the pharmaceutical art. The active drug components of the present invention are used in liquid, powdered or lyophilized form and may be combined with a suitable diluent or carrier, such as water, a saline, aqueous dextrose, aqueous buffer, and the like. Preservatives may also be added.

Regardless of the route of administration selected, the compounds of the present invention are formulated into pharmaceutically acceptable dosage forms by conventional methods known to those skilled in the art. The compounds may also be formulated using pharmacologically acceptable acid or base addition salts. Moreover, the compounds or their salt may be used in a suitable hydrated form.

Regardless of the route of administration selected, a non-toxic but therapeutically effective quantity of one or more compounds of this invention is employed in any treatment. The dosage regimen for treating is selected in accordance with a variety of factors including the type, age, weight, sex and medical condition of the patient, type of tumour, the route of administration and the particular compound employed in the treatment. A physician of ordinary skill can readily determine and prescribe the effective amount of the drug required regarding known antibody therapy approaches (Hale (1988), Cobbold (1990)). In so proceeding, the physician could employ relatively low doses at first, and subsequently, increased dose until a maximum response is obtained.

The chaotic over-expression of multiple spliced variants of the CD44 gene in tumours, implies that a particular exon may or may not be over-expressed (or expressed at all) by a particular tissue sample. An immunoassay using an antibody to the peptide expressed by any single exon may therefore give misleading results. This invention therefore includes use, for the immunological diagnosis of neoplasia, of a mixture of antibodies to two or more, and preferably to all nine, of the CD44 exons.

In the examples which follow it was found that expression of the human CD44 gene was consistently and distinctively increased in various solid tumours relative to normal tissues. Malignant (i.e. already metastatic) tumours differed from locally invasive and benign ones in the pattern and magnitude of changes seen. The study was performed on samples from 46 tumours of which 44 were locally invasive, or metastatic and 2 were benign. Analysis of CD44 expression was performed by using PCR to amplify cDNA made by reverse transcription of RNA extracted from fresh surgical biopsy samples. By choosing oligonucleotide primers which specifically anneal to certain portions of the CD44 gene, it is possible to amplify portions of the gene which, from these results, are of diagnostic and prognostic interest.

The strong association found here, between altered CD44 expression and neoplasia, need not imply that any of the individual exons of the gene are expressed only in neoplasia or in progression to metastatic malignancy. Evidence accrued in many laboratories in recent years (see Knudson 1985, Tarin 1992, Hayle et al 1992 for reviews) indicates that these pathological processes are probably the consequences of disturbed regulation of genes coding for normal cellular activities such as cell proliferation and migration. Therefore it seems unlikely that any gene, or portion of a gene, has the sole function of programming neoplasia or metastasis.

The finding in the present study of transcripts from exon 10/11 in normal tissues, indicates that this exon is not exclusively concerned with metastatic activity, even though there is marked increase in the number and signal intensity of bands hybridising with radiolabelled probe E4 in the PCR products from tumours capable of metastasis. Other supporting events are therefore believed to be required for CD44 exon 10/11 expression to result in metastatic behaviour. Nevertheless, the observation that transcripts from this exon were over-expressed in samples from metastatic tumours promises to be a very useful indicator of prognosis.

It is not expected that further research will find that the natural (non-mutated) products of any individual exon will be uniquely present in tumour cells and not in normal counterparts. Instead, it is likely that an abnormal pattern of gene activity consisting of over-expression and inappropriate combination of products of a gene, such as that reported here for the CD44 locus, could play a part in malignancy. These changes may themselves be required for malignant conversion, or be the consequence of other genetic disturbances causing such a conversion. Even so, without resolving this issue, an observer using these techniques can obtain information relevant to assigning a sample to neoplastic or non-neoplastic categories.

EXAMPLES

Method

Fresh tissue samples, 0.5–1 cm diameter, were obtained from surgical resection specimens removed at therapy of 34 patients with breast tumours and colon tumours. The samples were snap-frozen in liquid nitrogen within ten minutes of arrival in the pathological specimen reception area and kept in liquid nitrogen until use. Portions of lymph node metastases and blood-borne metastases were also collected, if present, in the tissue resected for diagnosis. Normal breast tissue, normal colon mucosa, normal lymph node adjacent to the tumour in the breast and normal liver were also collected from the surgically resected samples and from other samples removed for non-neoplastic conditions. Normal peripheral blood leukocytes were obtained from 10 volunteers and bone marrow from 3 volunteers. The histological features of the tumours and their clinical stages were as described in Table 1.

Total cellular RNA extraction from tissue samples was performed according to the method described by Chomizynski and Sacchi (1987). Extraction from fluid samples was by use of the Microfasttrack kit marketed by Invitrogen. cDNA synthesis and subsequent amplification by the polymerase chain reaction (PCR) was performed using the Superscript™ preamplification system (BRL Life Technologies Inc., Middlesex, UK) with buffers and reagents supplied in this kit. In brief, this involves an initial step of first strand cDNA synthesis with reverse transcriptase, using sample RNA as the template and supplied nucleotide triphosphates. For subsequent PCR each sample was overlaid with oil and heated at 94° C. for 5 minutes to denature nucleic acid; 30 cycles of PCR were then conducted with the following cycle parameters: 94° C. for 1 m, 55° C. for 1 m, 72° C. for 2 m. Negative controls in which there was no template cDNA in the reaction mix, were routinely run with each batch. The primers and probe sequences we devised, using information from the published sequence for human CD44 cDNA (Hofmann et al, 1991, Stamenkovic et al, 1991, Jackson et al, 1992) (FIG. 6) were as follows:

P1=5'GACACATATTGCTTCAATGCTTCAGC

P4=5'GATGCCAAGATGATCAGCCATTCTGGAAT

P1 is located with its origin 324bp upstream from the insertion site in the standard CD44 molecule (between nucleotides 782 and 783 in the sequence published by Stamenkovic et al, 1989) and P4 is 158 bp downstream of this site. These primers produce a PCR fragment of 482 bp if a sample expresses standard CD44 (so-called haemopoletic CD44), 878bp for the epithelial form of CD44 and several other bands, if a sample contains alternatively spliced transcripts. 10 μl of each PCR product was electrophoresed in a 1.2% agarose gel and transferred to Hybond N+ (Amersham UK, Little Chalfont, UK) nylon membranes for hybridisation with oligonucleotide probe E4 (=5'TGAGATTGGGTTGAAGAAATC-3'), see FIG. 6. Blotting and autoradiography were performed to improve sensitivity of detection and resolution. The probe was radiolabelled with $y^{32}P$-ATP in the presence of polynucleotide kinase. After prehybridisation, hybridisation was performed in 10% dextran, 6×NET, 5×Denhardt solution, 0.5% NP40 and 100 μg/ml salmon sperm DNA at 42° C. overnight. The filter was then washed twice in 2×SSC, 1×SSC and 0.5% SSC with 0.1% SDS at 42° C. sequentially for 15 minutes each. Filters were exposed to Kodak X-ray film for 2–16 hours. After this, the filters were boiled in 0.5% SDS for stripping the probe and rehybridised with another radiolabelled probe, namely P2 (=5'CCTGAAGAAGATTGTACATCAGTCACAGAC) we designed to anneal to the standard portion of the CD44 (FIG. 6). The conditions used for hybridisation, washing and autoradiography were the same as above.

Calibration of the sensitivity of the method, for detection of small numbers of cells was performed as follows: total peripheral blood leukocytes (PBL) were purified from 20 ml whole blood by lysis of packed red blood cells by addition of ammonium chloride buffer (1 ml packed cells to 50 mls lysis buffer) and subsequent centrifugation 15 minutes later. The white cell pellet was divided into 4 tubes which were seeded respectively with 0 μl, 1 μl, 10 μl and 100 μl of a suspension of HT29 colon carcinoma cells (5000 cells per ml). Total RNA was then extracted and each tube yielded approximately 20 μg. cDNA synthesis was performed, as described above on 4 μg aliquots of the RNA obtained from each tube representing 0, 1, 10 and 100 tumour cells per aliquotted sample respectively. The PCR was performed on these samples and on positive (tumour cells only) and negative (no DNA) controls using primers D1 and D5 which were designed by us to anneal specifically to exons 7 and 14 in FIG. 6. We know from previous studies that HT29 cells express both exons, and others, in a pattern easily distinguishable from PBL and chose the oligonucleotide primers D1 and D5 because we wished to increase sensitivity by shortening the segment to be amplified. It was also reasoned that use of these primers would circumvent the problem of using primers P1 and P4 for this specific purpose because the majority of these would be soaked up by annealing to the standard portion of the gene. PCR cycle parameters, blotting, probing and washing conditions were as described above. The oligonucleotide sequence used for probing was $^{32}$P labelled E4.

General Overview of Results

As the primers (P1 and P4) amplify across the splice product insertion site it is clear that the intervening part of the standard molecule will be amplified, in addition to any alternatively spliced variants which contain transcriptex- from the additional exon domains. Hence the total number of products which could conceivably be detected with a probe (e.g. P2) to the standard form considering all possible combinations of the sequences identified from this locus, is large. Using probe E4, 16 of these combinations, namely those containing E4 transcripts from exon 11, could potentially be visualised as bands of different molecular sizes resolved by electrophoresis. In practice the full range of possible combinations was not detected in these results, but several (up to 9) alternative splice variants were seen in neoplastic tissues hybridised with each probe. Normal tissues from the breast, colon and lymph nodes did express some E4-containing transcripts (FIGS. 1 and 3), in addition to the standard molecule (FIGS. 2 and 4), but peripheral blood leukocytes (FIG. 5) and liver (FIG. 4) detectably expressed only the latter with this combination of probes and primers. The details are presented below:

Example 1

Breast Tissue Samples

Figure 1A:
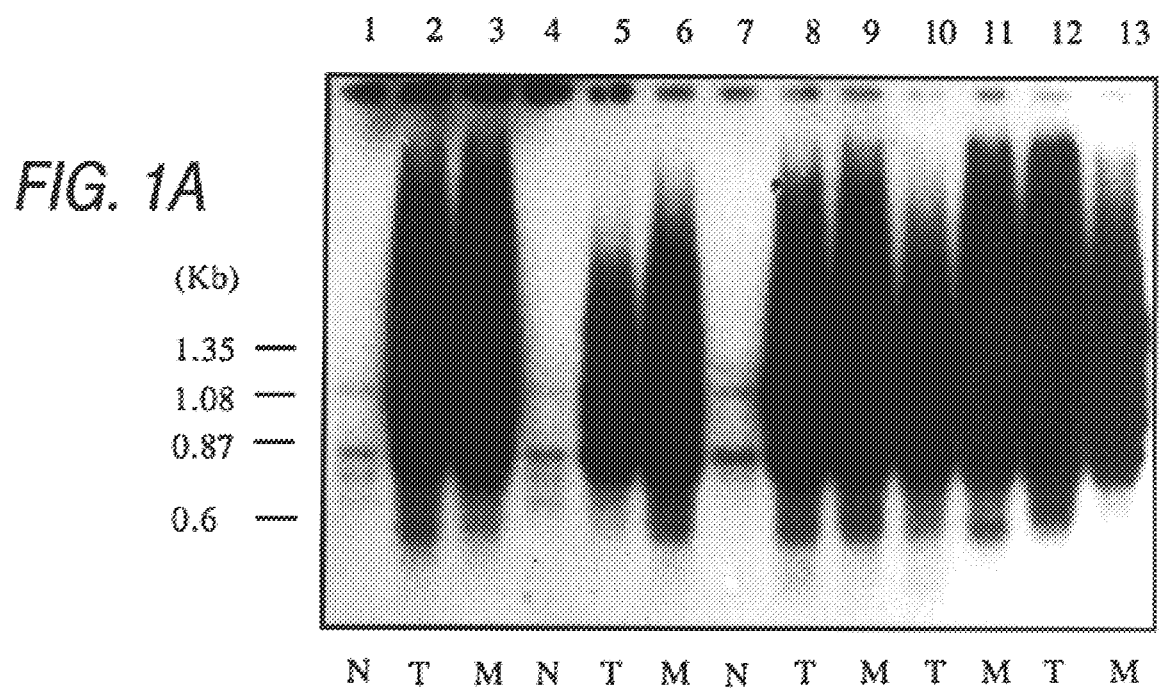
Figure 1B:
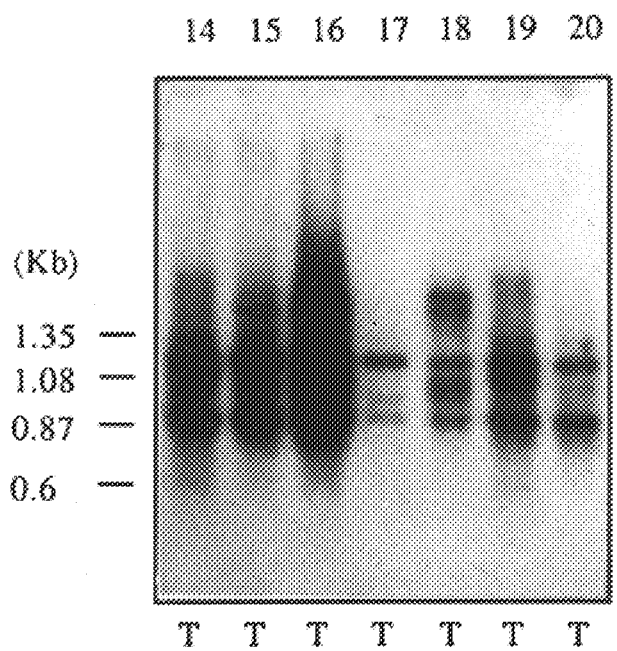
Figure 1C:
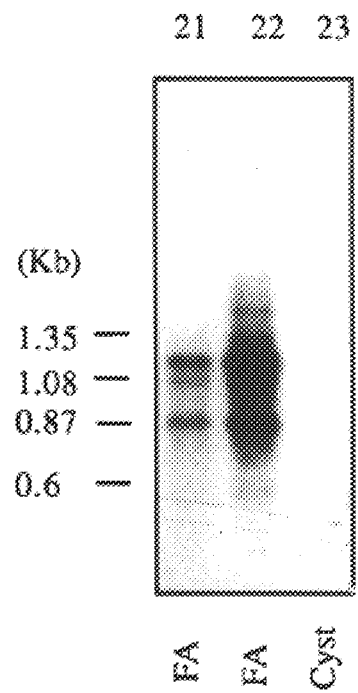
Figure 2A:
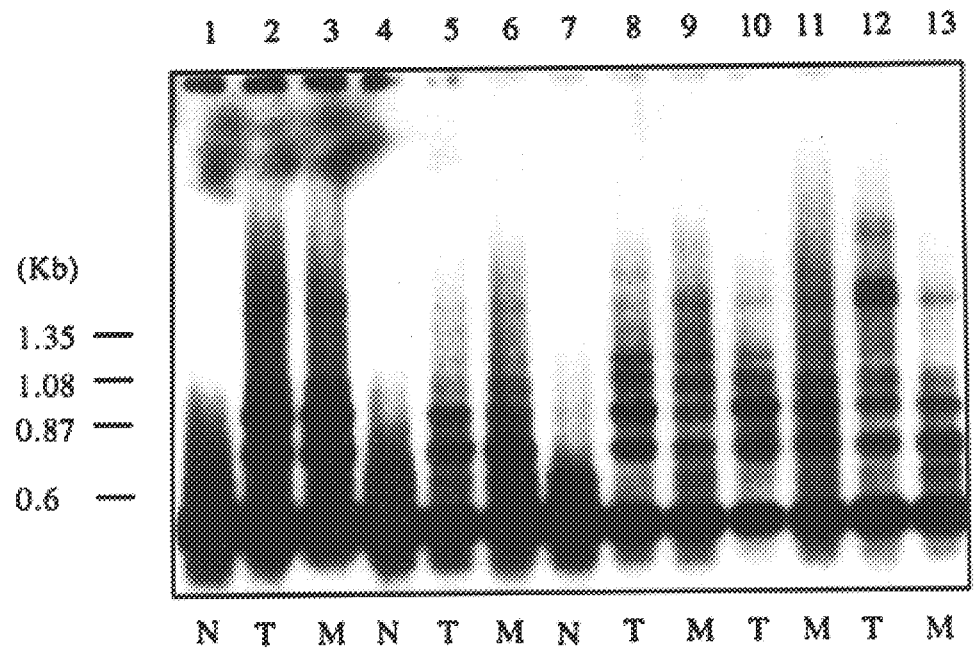
Figure 2B:
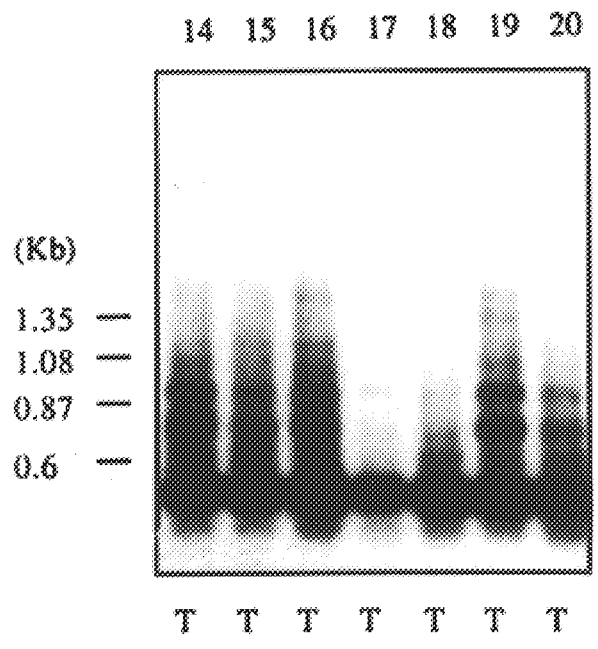
Figure 2C:
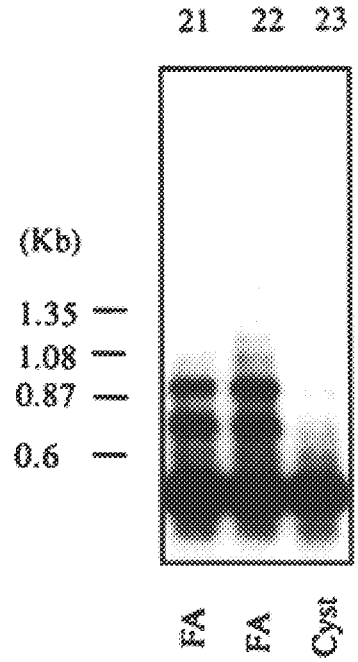
Figure 3:
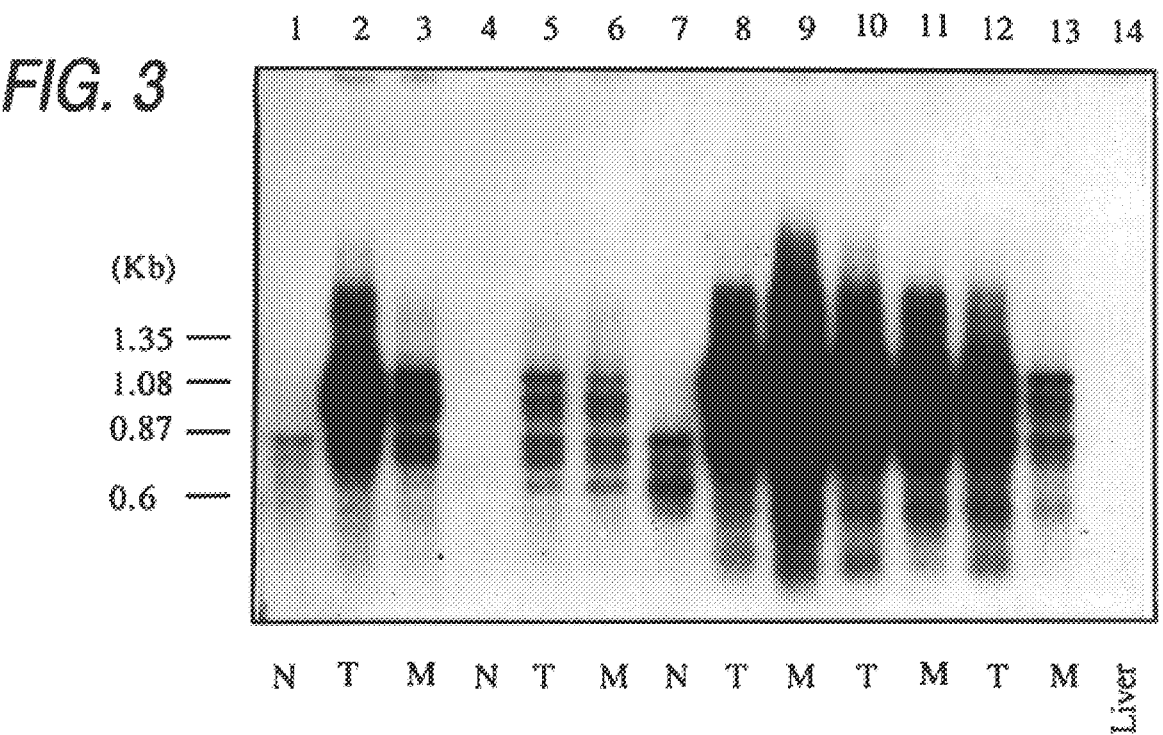

The results obtained in the study of breast tissue samples are illustrated in FIGS. 1 and 2. Metastatic tumour deposits and their corresponding primary tumours from all cases over-expressed several alternatively spliced products containing transcripts from exon 11 (FIG. 1a). At least 8 separate bands were frequently seen together with a consistent doublet at 1500 bp and 1650 bp present in all tumours. Normal breast tissue and normal lymph node produced two bands (1150 bp and 860 bp) with this probe. The doublet mentioned above was not seen in any normal sample.

The differences between the number, and size of the bands and the intensity of signal from the bound probe, between tissues in normal and malignant categories, was obvious in all samples examined. For occasional samples it was necessary to expose the filter to the X-ray film for longer, to see the distinctive differences, but this finding was confirmed in every case studied.

Samples from locally invasive tumours with no associated clinical evidence of metastasis and from the two fibroadenomas also over-expressed splice products containing transcripts from exon 10/11 relative to normal tissues, but the extent of this was easily distinguished from the results obtained with malignant tumours and their metastases. Distinction from the patterns seen in normal tissues was also easy (FIG. 1b). However, a single sample gave a similar result to malignant tumours (lane 14) (see below). The two fibroadenomas showed band patterns that were similar to those from non-metastatic carcinomas and the sample from a case of cystic disease of the breast resembled the pattern for normal non-neoplastic breast tissue. This is the first instance of definitive diagnosis by this method. The piece of tissue was provided by the duty pathologist as being from a benign tumour, namely a fibroadenoma, on macroscopic appearance at initial inspection with the naked eye. It was then characterised as definitely non-neoplastic after PCR amplification of its cDNA, and subsequent microscopical examination of the tissue confirmed this.

To confirm that the differences seen with probe E4 are valid and not technical artifacts, the results obtained when the same filter was hybridised with probe P2 are shown in FIG. 2. This shows that i) all tissues examined expressed the standard form of the gene, ii) other exon splice products, not containing transcripts from exon 10/11, were present in tumours and metastases and iii) that the differences described above are not due to unequal loading of tracks in the various panels and lanes on this composite filter, but resulted from alternative splicing. All conditions in this experiment were the same as those in hybridisation with E4, except the exposure time of the filter to X-ray film (10 hours exposure for FIG. 1, versus 1.5 hours for FIG. 3).

Example 2

Colon Samples

Figure 4:
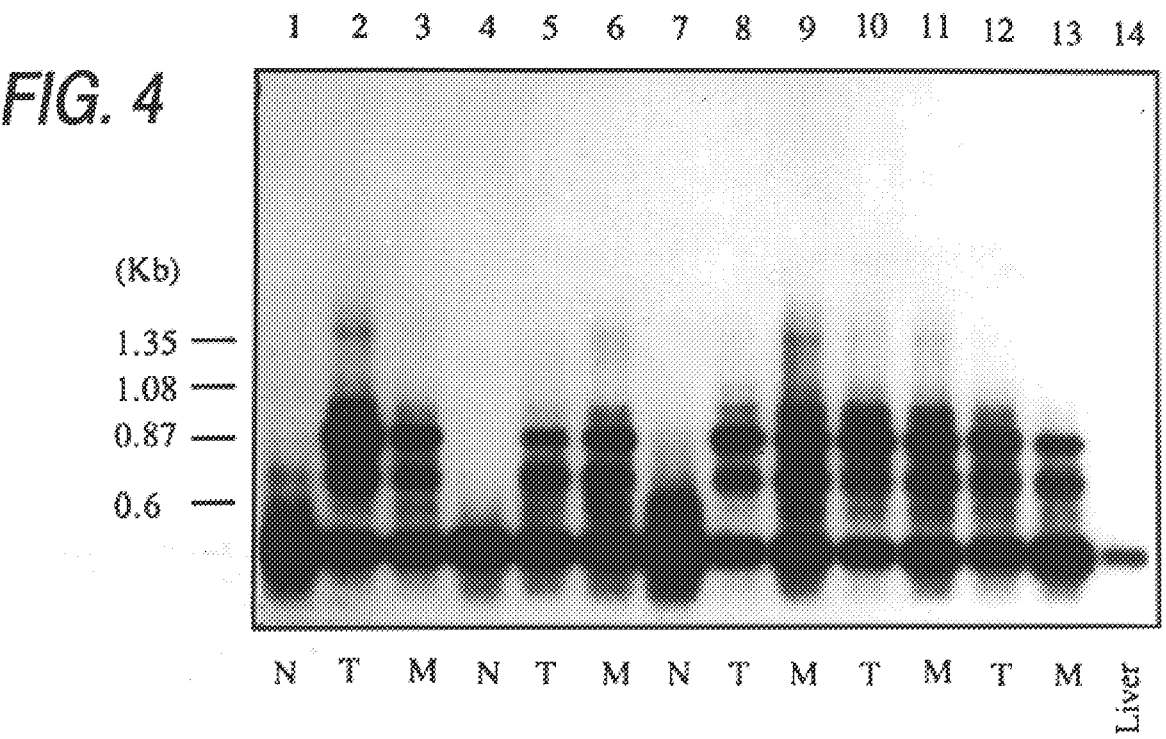

The findings in colon carcinoma were identical to those in breast carcinoma. Thus, in all cases the colon carcinoma tissues showed increased number of more intensely labelled, larger molecular weight bands with probe E4 (FIG. 3) than normal colonic mucosa and other normal tissues. As with breast carcinomas, hybridisation with probe P2 showed no differences in the degree of expression of the standard form of the molecule (FIG. 4).

Example 3

Calibration of the Sensitivity of the Method

Examination of autoradiograms of PCR products of peripheral blood leukocytes seeded with known numbers of HT29 colon carcinoma cells showed the presence of additional bands characteristic of tumour cells, down to a level of 10 tumour cells in a sample of $10^7$ leukocytes. By fine-tuning the conditions of the assay it is considered possible to detect a single tumour cell in 10 ml of blood.

In the series described above, all samples of neoplastic tissue showed over-expression of alternatively spliced products of the CD44 gene and none of the samples from non-neoplastic tissue did so. Therefore, there was complete correspondence between normal or neoplastic origin of a sample and pattern of CD44 expression. In one instance, a tumour removed from a patient (patient B16, lane 14 in FIG. 1A) with no current clinical evidence of metastasis, was found to have a pattern of expression indicating metastatic capability. At present it is not possible to know whether this is a false positive result, or a sign of imminent metastasis. This patient is currently under observation in the follow-up clinic.

Example 4

We have designed and synthesised oligonucleotide primers according to our current findings, as follows:

Primer P1=5'-GACACATATTGCTTCAATGCTTCAGC (458–484)

Primer P2=5'-CCTGAAGAAGATTGTACATCAGTCACAGAC (488–518)

Primer P3=5'-TGGATCACCGACAGCACAGAC (746–767)

Primer P4=5'-GATGCCAAGATGATCAGCCATTCTGGAAT (912–941) for standard part (Stamenkovic 1989)

Primer E1=5'-TTGATGAGCACTAGTGCTACAGCA

Primer E2=5'-CATTTGTGTTGTTGTGTGAAGATG

Primer E3=5'-AGCCCAGAGGACAGTTCCTGG (534–554)

Primer E4=5'-TGAGATTGGGTTGAAGAAATC (558–578)

Primer E5=5'-TCCTGCTTGATGACCTCGTCCCAT (585–608)

D1: 5' GAC AGA CAC CTC AGT TTT TCT GGA (63–86)

D5: 5' TTC CTT CGT GTG TGG GTA ATG AGA (888–911)

for the exons (Hofmann 1991). E1 and E2 are on exon 6.

Fresh tissue samples 0.5–1 cm in diameter were obtained from surgical resection specimens or at autopsy. All samples used in this work were obtained from the residue of tissue remaining after diagnostic samples had been taken, and which would otherwise have been discarded. The samples were snap-frozen in liquid nitrogen within ten minutes of arrival at the pathological specimen reception area and kept frozen in nitrogen until use. cDNA was synthesised with viral reverse transcriptase using 5 µg of total cellular RNA as template, followed by PCR with Primer P1 and Primer P4. PCR amplification, electrophoresis and hybridisation were performed under standard conditions.

When the PCR products were hybridised with radiolabelled E2 or E4, all samples from carcinomas overexpressed several splice variants, but the pattern of bands seen with each probe was different. Hence, the oligonucleotide probe for Exon 6 products is very effective in distinguishing neoplastic from non-neoplastic samples, but not significantly more sensitive than E4, at least on samples from solid tissues, but is possibly useful for detecting organ of origin of a disseminating metastatic cell or an established metastasis. Subsequently, the same filters were stripped and hybridised with P2 probe to show that all samples, including normal tissues, produced the standard portion of CD44. This confirmed that the differences observed between the results obtained with normal and tumour samples, probed with E2 and E4, were not due to unequal loading of PCR products. The cumulative results are summarised in Table 3 which indicates that these changes are seen in a wide range of common cancers.

TABLE 3

| Type of Tissue | No. of Patients/ Volunteers | No. Showing Increased Splice Variants |
|---|---|---|
| Neoplastic | 47 | 46 |
| Breast Cancer | 21 | 21 |
| Colon Cancer | 13 | 13 |
| Bladder Cancer | 6 | 6 |
| Stomach Cancer | 1 | 1 |
| Thyroid Cancer | 1 | 1 |
| Fibroadenoma | 2 | 2 |
| Prostate Cancer | 3 | 2 |
| Non-Neoplastic | 39 | 0 |
| Normal Breast | 9 | 0 |
| Cystic Disease of Breast | 1 | 0 |
| Normal Colon | 9 | 0 |
| Crohn's Disease | 1 | 0 |
| Ulcerative Colitis | 1 | 0 |
| Appendicitis | 1 | 0 |
| Normal Bladder | 4 | 0 |
| PBL | 10 | 0 |
| Bone Marrow | 3 | 0 |

We have also examined some malignant tumours of bone muscle and observed a similar pattern, of marked overexpression of multiple spliced variants, in the osteosarcoma.

Example 5
Cancer Diagnosis by PCR Assay of Clinically-Harvested Urine Samples

Approximately 50 ml naturally-voided urine were obtained from each person and transported to the laboratory as speedily as possible. Specimens from 90 patients were examined: 44 from patients with biopsy-proven bladder cancer, 46 from patients with non-neoplastic inflammation of the bladder (cystitis) and from normal volunteers. One ml of each urine sample was removed after thorough mixing and submitted for cytological examination. Another 1 ml of urine was checked by Fluorescein diacetate-ethidium bromide staining to assess the viability of cells in the sample. The remainder of the urine was centrifuged at 2000 rpm for 10 minutes and the cell pellet was kept at −70° C. until use. mRNA extraction was performed with oligo dT cellulose tablets (invitrogen). cDNA was synthesised with AMV reverse transcriptase (Invitrogen). The completed cDNA solution was divided equally into two tubes, one being for PCR with E1 and E5, to amplify the particular cDNA transcript, which we have found to be of diagnostic value and the other for PCR with P1 and P4 to amplify the standard form of CD44, with or without all splice variants, as an internal control.

Thirty-five cycles PCR were then carried out. The cycle conditions were: 95° C. 1 minutes, 55° C. 1 minute, 72° C. 2 minutes. A hot start procedure was adopted for all samples. Results are shown in FIG. 8.

Equal volumes of PCR products were loaded in each lane of a 1.2% agarose gel and stained with ethidium bromide. If the cells in the urine were to be expressing all the Exons from Exon 6 to Exon 14, it was predicted that with the current PCR protocol, using primers E1 and E4, should produce a 735 bp band. There is no band in tracks containing cDNA from normal urine or that of patients with non-neoplastic cystitis (lanes 1–8) but a clear 735 band is seen in all urine samples from patients with bladder cancer (lanes 9–16) when PCR was performed with primer E1 and E5 (upper panel).

A 482 bp band representing the standard form of CD44 was obtained almost equally in all cases when PCR was performed with P1 and P4 (lower panels). This indicates that the diagnostically significant differences between urine from patients with bladder cancer and that from controls were not caused by unequal loading of the tracks but by alternative splicing of the CD44 gene. Lanes 1–4: normal urine. Lanes 5–8: cystitis urine. Lanes 9–16: from patients 1–8 with bladder cancer.

In the overall results this 735 bp band was completely absent in 7 of 7 normal and 9 of 9 cystitis-affected urine specimens; that is 0% false positive. Also 14 of 19 (74%) urine samples from patients with bladder cancer showed a positive result (i.e. 26% false negatives). In the false negative samples there was a shortage of viable cancer cells as indicated by fluorescein-d acetate ethidium bromide staining.

Example 6

Stools from 12 patients were assayed by the techniques described herein. Of the samples from 9 patients with colorectal carcinoma, 5 gave positive results. Of the samples from 3 normal patients, all 3 gave negative results. These figures, obtained from samples full of bacteria which were not subjected to any pretreatment, encourage the belief that a viable diagnostic assay could be developed without difficulty.

In the inventors' further experience of detecting tumour cells with this method, the following observations would be useful to others investigating its diagnostic potential. The major considerations to be aware of are that the reliability and reproducibility of the results depend critically on the quality of the mRNA obtained from the sample and upon the care with which the techniques are performed. The main requirement is to eliminate false negative results by ensuring that high quality mRNA is routinely obtained and by using internal standards in every reaction to monitor the PCR amplification step. False positives, providing they are not too frequent, are not a serious problem, because they can be recognised by replicate assays on the same or further samples and by reference to other clinical data.

The inventors have explored the procedures needed to ensure the routine RT-PCR detection of abnormal CD44 gene activity in small clinical samples containing tumour cells. If a tissue sample is divided into aliquots, half of which are frozen in liquid nitrogen immediately and the remainder of which are left at ambient temperature, one can show how the ability to detect CD44 splice variants declines with time and with mode of specimen handling. Fresh samples submitted to mRNA extraction within half an hour of excision give the most reliable results and there is a gradual decline in quality over the next few hours if the fresh tissue is left at ambient temperature. If the sample is first snap frozen, the results obtained when RNA is extracted immediately after thawing are satisfactory, but decline very rapidly, beginning within 15 minutes, the larger variant transcripts being lost first and ultimately even the standard form. It is also found that if snap-frozen cell and tissue samples are stored at −70° C. the results decline after 4 weeks, even if the mRNA is extracted immediately after thawing. It would seem therefore that degradation of RNA by ribonucleases released from cells ruptured during freezing continues, even at this temperature, although at slower rates. Further, as one would expect, if the sample taken for RNA extraction is from an area of necrosis or of fibrosis, one does not obtain the typical results seen with viable tumour tissue. Hence, care in sample selection and in specimen processing are both needed for generating reliable data.

Arising out of this, we prefer that a fresh sample should be held for not more than 24 hrs before being either frozen or treated to extract mRNA; and that a thawed sample should be held for not more than 2 hrs before being treated to extract mRNA.

The diagnosis method described herein can be performed in a single day, possibly in a few hours, and is capable of being automated. Use of the method has been demonstrated, on various tissue samples to detect a whole variety of cancers, and also on blood and urine samples. We therefore offer it as a convenient practical method for cancer screening and diagnosis. In principle it could also have wide general applicability to cancer detection and prevention programmes and therefore have epidemiologic and public health value. Proper application of its sensitivity, specificity and simplicity should add not only to initial cancer diagnosis but to evaluation of extent of disease in the body, to judgment of the efficacy of treatment and to early detection of tumour recurrences.

FIGURE LEGENDS

Notation: N=normal, T=primary tumour, M=metastasis.

FIG. 1

Autoradiogram of PCR products from breast tissue samples probed with E4 (10 hours exposure of X-ray film to sample filter). Panel A: malignant primary breast carcinomas with their metastases. Tracks 1, 2 and 3: patient B1; tracks 4, 5 and 6: patient B2; tracks 7, 8 and 9: patient B3; tracks 10 and 11: patient B4; tracks 12 and 13: patient B5. It can be seen that compared to normal breast tissue, primary breast carcinomas and their metastatic deposits overexpress several splice-variants. Note the doublet (arrows) at 1500 bp and 1650 bp best seen in track 5. This is present in all tumours and metastases but is fogged in the other tracks by this time of exposure. It is not detectable in any normal samples even at much longer exposure times (23 hours). Panel B: Breast carcinomas with no clinical evidence of metastasis. Tracks 14–20 are from patients B15–B21. The tumours all overexpress several variants, but show less bands and the signal intensity is less, except track 16 (patient B17)—see text. The 1500/1650 bp doublet (arrow) is easily recognisable in tracks 15, 16 and 18 at this length of exposure and became detectable in all other tumour-containing tracks on longer exposure. The illustration, however, shows only the shorter exposure, to avoid fogging the tracks which have stronger signals. Panel C: Fibroadenomas (FA) and fibrocystic disease of the breast (Cyst). Tracks 21 and 22, containing the benign tumour samples (samples B22 and 23), express more than the non-neoplastic sample (fibrocystic disease) in track 23 (sample B24).

FIG. 2

Autoradiogram of PCR products from breast tissue samples probed with probe P2 (1.5 hours exposure of X-ray film to sample filter). This result was obtained by reprobing the same filter as that used in FIG. 1, after stripping off the previous probe. Here it can be seen that i) the differences observed in FIG. 1 are not due to unequal loading of tracks, ii) that the expression of the standard form of the molecule is quantitatively greater than any of the variants, iii) the standard form is expressed in all tissues examined and iv) further variants which do not contain exon 3 transcripts, are also present and over-expressed in tumours. The 1500/1650 bp doublet can be recognised in the tumours in panel A but needed longer exposure to be detectable in panels B and C.

FIG. 3

Autoradiogram of PCR products from colon tissue samples probed with E4 (10 hours exposure of photographic film to sample filter). Tracks 1, 2 and 3: patient C1; tracks 4, 5 and 6: patient C2; tracks 7, 8 and 9: patient C3; tracks 10 and 11: patient C4; tracks 12 and 13: patient C5; track 14: normal liver sample. The picture shows the same features as described in the legend to FIG. 1 and that the findings apply to carcinomas of the colon. The 1500/1650 bp doublet (arrow) is easily recognisable in several tumour tracks (2 and 8–12) and the faint signal in the corresponding position in tracks 3, 5, 6 and 13 became stronger on longer exposure. However none appeared in this vicinity in tracks 1, 4, 7 or 14 (normal tissue).

FIG. 4

Autoradiogram of PCR products from colon tissue samples probed with P2 (1.5 hours exposure of photographic film to sample filter). This confirms equal loading of the tracks and that other points, illustrated in FIG. 2, apply to colon carcinomas. Note that normal liver expresses the standard form of CD44.

FIG. 5

Autoradiogram of PCR products of normal peripheral blood leukocytes, PBL (from 3 different persons) and other normal tissues probed with E4 (panel A; 8 hours exposure to photographic film) and P2 (panel B; 5 hours exposure to photographic film). Track 6 contains PCR products from a breast cancer (patient B1) as a positive control. With this combination of primers and probes, leukocytes can be seen to express the standard form of the CD44 molecule, but no detectable splice variants. The samples in tracks 4 and 5 were from individuals with no clinical evidence of neoplasia, as follows: track 4, breast tissue obtained at autopsy from the body of a woman who died of bacterial endocarditis; track 5, colon resected for volvulus.

TABLE 1

| PATIENT | AGE | DISEASE | TUMOUR SIZE | METASTASIS | HISTOLOGY (GRADE) | CLINICAL STAGE |
|---|---|---|---|---|---|---|
| B1 | 56 | Breast ca | 2.5 cm | Lymph node | | |
| B2 | 53 | Breast ca | 3 cm | Lymph node | | |
| B3 | 65 | Breast ca | 3 cm | Lymph node | | |
| B4 | 54 | Breast ca | 5 cm | Lymph node (10/10) | IDC (mucinous) [1] | |
| B5 | 59 | Breast ca | 5.5 cm | Lymph node | | |
| B6 | 59 | Breast ca | 3 cm | Lymph node | | |
| B7 | 61 | Breast ca | 4 cm | Lymph node (17/17) | ILC/IDC | 3 |
| B8 | 38 | Breast ca | 3.5 cm | Lymph node (1/5) | ILC | 2 |
| B9 | 65 | Breast ca | 1.8 cm | Lymph node (5/6) | ILC | 2 |
| B10 | 61 | Breast ca | | Lymph node (10/13) | IDC [1] | 2 |
| B11 | 80 | Breast ca | 11 cm | Lymph node | 3 | |
| B12 | 65 | Breast ca | 2.3 cm | Lymph node | ? 1 | |
| B13 | 68 | Breast ca | 2.8 cm | Lymph node (4/12) | IDC [3] | 2 |
| B14 | 47 | Breast ca | 7 cm | Lymph node | | 2 |
| B15 | 38 | Breast ca | | None (0/7) | IDC | 1 |
| B16 | 62 | Breast ca | 3 cm | None (0/4) | IDC [3] | 1 |
| B17 | 62 | Breast ca | 3 cm | None (0/16) | IDC [2] | 1 |
| B18 | 63 | Breast ca | 3 cm | None (0/16) | 1 | |
| B19 | 61 | Breast ca | 3 cm | None | 1 | |
| B20 | 42 | Breast ca | 4 cm | None | IDC | 1 |
| B21 | 65 | Breast ca | | Lymph node | IDC/ILC | |
| B22 | 54 | Breast ca | 6 cm | None (0/4) | IDC | 1 |
| B23 | 49 | Fibroadenoma | 4 cm | — | — | — |
| B24 | 47 | Fibroadenoma | 3 cm | — | — | — |
| B25 | 29 | Cystic disease | — | — | — | — |
| C1 | 72 | Colon ca | 5.0 cm | Lymph node | Well diff. adeno | 3 [C] |
| C2 | | Colon ca | | Lymph node | | |
| C3 | 65 | Colon ca | 6.5 cm | Liver | Mod diff. adeno | 4 [D] |
| C4 | 56 | Colon ca | 7.8 cm | Lymph node | Mod diff. adeno | 4 [D] |
| C5 | | Colon ca | | Lymph node | | |
| C6 | 57 | Colon ca | 5 cm | Lymph node | Mod diff. adeno | 3 [C] |
| C7 | | Colon ca | | None | | |
| C8 | 75 | Colon ca | 6.5 cm | Lymph node | Mod diff. adeno | 3 [C] |
| C9 | 72 | Colon ca | 5.5 cm | Lymph node | Mod diff. adeno | 3 [C] |
| C10 | 76 | Colon ca | 4.5 cm | None | Well diff. adeno | 1 [B] |
| T1 | | Thyroid ca | | | | |

Key:
IDC: infiltrating ductal carcinoma
ILC: infiltrating lobular carcinoma
Well diff. adeno: Well differentiated adenocarcinoma
Mod diff. adeno: Moderately differentiated adenocarcinoma
Letters in square brackets in Clinical Stage column refer to Dukes staging scheme for colon carcinoma

REFERENCES

1. Stamenkovic, Amiot M, Pesando J. M, Seed B. A lymphocyte molecule implicated in lymph node homing is a member of the cartilage link protein family. Cell 1989; 56: 1057–062.
2. Birch M, Mitchell S, Hart I. R. Isolation and characterisation of human melanoma cell variants expressing high and low levels of CD44. Cancer Res. 1991; 51: 6660–6667.
3. Gunthert U, Hofmann M, Rudy W, Reber S, Zoller M, HauBmann, Matzku S, Wenzel A, Ponta H, Herrlich P. A new variant of glycoprotein CD44 confers metastatic potential to rat carcinoma cells. Cell 1991; 65: 13–24.
4. Sy M S, Guo Y-J, Stamenkovic I. Distinct effects of two CD44 isoforms on tumor growth in vivo. J. Exp. Med 1991; 174: 859–866.
5. Hofmann M, Rudy W, Zoller M, Tolg C, Ponta H, Herrlich P, Gunthert U. CD44 splice variants confer metastatic behaviour in rats: Homologous sequences are expressed in human tumor cell lines. Cancer Res. 1991; 51: 5292–5297.
6. Stamenkovic I, Aruffo A, Amiot M, Seed B. The hematopoletic and epithelial forms of CD44 are distinct polypeptides with different adhesion potentials for hyaluronate-bearing cells. EMBO J. 1991; 10: 343–348.
7. Jackson D. G, Buckley J, Bell J. I. Multiple variants of the human lymphocyte homing receptor CD44 generated by insertions at a single site in the extracellular domain. J. Biol. Chem. 1992; 267: 4732–4739.
8. Chomzynski P, Sacchi N. Single-step method of RNA isolation by acid guanidinium thiocyantat-phenol-chloroform extraction. Anal Biochem. 1987; 162: 156.
9. Knudson A. G. Hereditary cancer, oncogenes and anti-oncogenes. Cancer Res. 1985; 45: 1437–43.
10. Tarin D. Tumour metastasis. In: Oxford Textbook of Pathology 1992; (eds: J O'DMcGee, N. A. Wright, P. G. Isaacson). Oxford University Press, Oxford. pp607–633.
11. Hayle A. J, Darling D. L, Taylor A. R, Tarin D. Transfection of metastatic capability with total genomic DNA from metastatic tumour cell lines. Differentiation, 1993, in press.
12. Screaton G. R., Bell M. V., Jackson D. G., Cornelis F. B., Gerth U., and Bell J. I., Genomic Structure of DNA encoding the lymphocyte homing receptor CD44 reveals at least 12 alternatively spliced exons, Proc. Natl. Acad. Sci. USA, Vol 889, p 12160–4, December 1992, Immunology.

Example 7

I. Peptide Synthesis 5 peptides corresponding to amino acids 1–13, 9–23, 19–33, 29–43 and 1–43 of the peptide sequence corresponding to CD44 exon 6 as shown in FIG. 7 were synthesized by 9-fluoroenylmethyloxycarbonyl (Fmoc) chemistry solid phase peptid synthesis (Atherton and Sheppard, 1989) on an Applied Biosystems, Inc., Model 431A Peptid Synthesizer using the proprietor's standard scale (0.25 mmol) Fmoc chemistry option. For this purpose, 403 mg 4-(2', 4'-dimethoxyphenyl-Fmoc-aminomethyl)-phenoxy resin (Rink, 1987) with a substitution of 0.62 mmol/g resin are used. The amide resin is deprotected (Fmoc cleavage) by treatment with 20% piperidine in N,N-dimethyl formamide (DMF) before the first coupling cycle. For peptide synthesis, a 4-molar excess of the following Fmoc-amino acid derivatives and other carboxylic acids is used:

N-Fmoc-L-alanine
N-α-Fmoc-N$^G$-(2,2,5,7,8-pentamethylchroman-6-sulfonyl)-L-arginine
N-α-Fmoc-N-β-(trityl)-L-asparagine
N-α-Fmoc-L-aspartic acid-β-t-butyl ester
N-Fmoc-S-trityl-L-cystein
N-α-Fmoc-N-gamma-(trityl)-L-glutamine
N-α-Fmoc-L-glutamic acid-gamma-t-butyl ester
N-α-Fmoc-N-im-trityl-L-histidine
N-Fmoc-L-leucine
N-α-butyloxycarbonyl-N-ε-Fmoc-L-lysine
N-α-Fmoc-N-ε-butyloxycarbonyl-L-lysine
N-Fmoc-L-norleucine
N-Fmoc-L-phenylalanine
N-Fmoc-L-proline
N-Fmoc-O-t-butyl-L-serine
N-Fmoc-O-t-butyl-L-threonine
N-α-FMoc-N-ε-butylocxycarbonyl-L-tryptophan
N-Fmoc-gamma-aminobutyric acid
N-Fmoc-ε-aminocaproic acid
(+)-Biotin Prior to coupling, the amino acid derivatives are dissolved in DMF and activated through the addition of 1 equivalent N-hydroxybenzotriazole (HOBt) in N-methylpyrrolidinone (NMP) and 1 equivalent N,N'-dicyclocarbodiimide (DCC) in NMP. The 20-minute couplings of the HOBt-ester amino acid are carried out in DMF. Following coupling, deprotection of the N-termini (Fmoc cleavage) is achieved by a 3-minute and then a 10-minute treatment with 20% piperidine in DMF. The peptide chain is extended through repetition of the activation/coupling/deprotection cycles. Peptides utilized later for immunogen synthesis are outfitted with an N-terminal aminocaproic acid spacer and cystein, through which the peptide is tethered to the carrier protein. For peptides used as screening reagents, a different N-terminus is synthesized and contains three gamma-aminobutyric acid moieties, lysine, and biotin (attached to the ε-amino group of lysine). Following synthesis, the peptide is removed from the resin support by trifluoroacetic acid (TFA) cleavage. The peptide-bearing resin is reacted for 1 hour at room temperature (RT) with a cleavage cocktail containing 20 mL trifluoroacetic acid, 1 mL H$_2$O, 1 mL thioanisole, 0.5 mL ethanedithiol and 1.5 g phenol. Removal of the acid-labile side-chain protecting groups, performed under Argon, is complete after an additional 2.4 h reaction time at RT in the aforementioned cocktail solution. After a brief cooling period, the deprotected peptide is precipitated through the addition of diisopropylether. The precipitate is filtered, washed with diIsopropylether, dissolved in 50% acetic acid, frozen and lyophilized. Peptide purity is determined by reverse-phase HPLC (column—Vydac 218TP54, C$_{18}$, 300 Å, 5 μm, 4.6×250 mm; mobile phase—A: 0.1% TFA in H$_2$O, B: 0.1% TFA in H$_2$O/acetonitrile (35/65, v/v); gradient—0–100% B in 90 min; flow rate—1 mL/min; detection—226 nm). Those peptides being less than 60% pure are purified by reverse-phase HPLC (column—Waters DeltaPak C$_{18}$, 100 Å, 15 μm, 50×300 mm; mobile phase—A: 0.1% TFA in H$_2$O, B: 0.1% TFA in H$_2$O/acetonitrile 35/65, v/v, gradient—0.50% B in 130 min; flow rate—15 mL/min; detection—226 nm). Peptide identity is verified by plasma desorption mass spectrometry. Characteristic HPLC retention times and mass spectral data for the peptides used for immunogen synthesis are listed in Table 2.

TABLE 2

HPLC and MS Characteristics of Activated Hapten Peptides

| Peptid Name | Sequence[1] | Theoret. mass | Exp. mass (MH+) | Exp. Theoret | Retention time (min)[2] |
|---|---|---|---|---|---|
| AH,CD44(AT1-13NH$_2$,1-ZC) | H-CZATTLJSTSATAT ETA-NH$_2$ | 1651.76 | 1653.3 | +1.54 | 36.01 |
| AH,CD44(9-23NH$_2$,9-ZC) | H-CZATETATKRQETW DWF-NH$_2$ | 2155.31 | 2155.8 | +0.49 | 45.29 |
| AH,CD44(19-33NH$_2$,19-ZC) | H-CZTWDWFSWLFLPS ESK-NH$_2$ | 2214.47 | 2215.7 | +1.23 | 61.73 |
| AH,CD44(29-43NH$_2$,29-ZC) | H-CZPSESKNHLHTTT QJA-NH$_2$ | 1950.15 | 1950.5 | +0.35 | 28.92 |
| AH,CD44(1-43NH$_2$,1-ZC) | H-CZTLJSTSATATETA KRQETWDWFSWLFLP SESKNHLHTTTOJA-NH$_2$ | 5150.5 | 5149 | −1.50 | 57.64 |

[1]J = norleucine, 2, = aminocaproic acid, other abbreviations from standardized one-letter code.
[2]Retention times obtained using aforementioned HPLC conditions.

II. Activation of Carrier Protein

For immunogen synthesis, a carrier protein, either Keyhole Limpet Hemocyanin (KLH) or Bovine Serum Albumin (BSA), is modified through the ε-amine of lysines with the heterobifunctional cross-linking reagent, N-succinimidyl 3-maleimidopropionate (MPS). This imparts the carrier protein with "handles" onto which the sulfhydryl peptides are later conjugated. For the case of KLH, a 10 μM KLH solution is prepared with 0.1M NaHCO$_3$, pH 8.35. The pH of the suspension is adjusted to 8.3 and briefly centrifuged. After determining the protein concentration by the bicinchoninic acid (BCA) protein assay (Smith, et al., 1985), 3000 equivalents of a 0.3M MPS solution in dimethylsulfoxide are added dropwise to the stirred KLH solution and allowed to react at RT for 1 hour. The solution pH is adjusted to 7.0 with 0.1M HCl, and activated carrier protein is separated from excess MPS by size-exclusion chromatography (column—AcA 202, IBF Biotechnics, 5×12 cm, RT; buffer—0.1M $KH_2PO_4/K_2HPO_4$ pH 7.0, 0.1M NaCl; flow rate—6 mL/min, detection—226 nm). Protein concentration is again determined by the BCA Protein assay and the degree of maleimido-propionamide (MP) substitution of the activated KLH (KLH-MP) is determined with the Ellman's reagent, DTNB (Ellman, 1959). For BSA, a 190 $\mu$M BSA solution is prepared in 0.1M $KH_2PO_4/K_2HPO_4$ pH 7.0, to which is added dropwise 100 equivalents MPS (40 mM in 1,4-dioxane). After stirring the reaction mixture for 2 hours at RT, it is loaded onto a size-exclusion column. The activated BSA (BSA-MP) is purified and analysed analogous to KLH-MP. Substitution values of 20–35:1 and 200–600:1 are routinely achieved for the activated carrier proteins, BSA-MP and KLH-MP, respectively.

III. Conjugation of Peptide with Activated Carrier Protein.

Through formation of a thioether bond, thiol-containing peptides are conjugated with the MP-activated carrier protein. In the case of BSA-MP, a 74 $\mu$M BSA-Mp solution in 0.1M $KH_2PO_4/K_2HPO_4$ pH 7.0 is reacted with 1 equivalent (with respect to MP) of a 4 mM peptid solution in the same phosphate buffer. The solution is stirred slowly and allowed to react at RT overnight. After centrifugation, the soluble BSA-MP-peptide conjugate is separated from unbound peptide via size-exclusion chromatography (same chromatography conditions as given in section II). Analyses of the protein conjugate include protein concentration determination via BCA, as well as ascertaining the remaining number of unreacted MP-groups with Ellman's reagent. KLH-MP-peptide conjugates are synthesized similarly with the exception of activated carrier protein and peptide concentrations, which are 3 $\mu$M and 18 $\mu$M, respectively.

REFERENCE

Atherton, E. and Sheppard, R. C. (1989) Solid Phase Peptide Synthesis: A Practical Approach, Oxford, U. P., Oxford.

Ellman, G. L. (1959) Arch. Biochem. Biophys. 82, 70–77.

Rink, H. (1987) Solid-Phase Synthesis of Protected Peptide Fragments Using a Trialkoxydiphenylmethylester Resin. Tetrahedron Letters 28, 3787–3790.

Smith P. K., Krohn, R. I., Hermanson, G. T., Mallia, A. K., Gartner, F. H., Provenzano, M. D., Fujimoto, E. K., Goeke, N. M., Olson, B. J. and Klenk, D. C. (1985) Measurement of Protein Using Bicinchoninic Acid Anal. Biochem. 150, 76–85.

ABBREVIATIONS

BCA—bicinchoninic acid
BSA—bovine serum albumin
BSA-MP—bovine serum albumbin activated with N-succinimidyl 3-maleimidopropionate
DCC—N,N'-dicyclocarbodiimide
DMF—- N,N-dimethylformamide
DTNB—dithio-bis-(2-nitrobenzoic acid), Ellman's reagent
Fmoc—9-fluorenylmethyloxycarbonyl
HOBt—N-hydroxybenzotriazole
KLH—Keyhole Limpet hemocyanin
KLH-MP—Keyhole Limpet hemocyanin activated with N-succinimidyl 3-maleimidopropionate
MP—maleimidopropionamide
MPS—N-succinimidyl 3-maleimidopropionate
NMP—N-methylpyrrolidinone
RT—room temperature
TFA—trifluoroacetic acid Example 8

Manufacture of the recombinant HIV2 (gp32)-CD44 exon 6 antigen/immunogen

Exon 6 of the CD44 gene codes for a peptide of 43 amino acids as shown in FIG. 7.

Peptides and small proteins of less than 100 amino acids as a rule cannot be made recombinantly by cytoplasmic expression in a microorganism. For this reason, a fusion gene comprising a gene which is readily expressible in *E. coli* (part of the envelope protein gp32 of the HIV2 retrovirus) and CD44 exon 6-DNA was constructed.

To increase the CD44 exon 6 epitopes in the fusion protein, the CD44 exon 6 antigen was duplicated at the DNA level using a suitable linker (codes for the 3 C-terminal amino acids of the exon 5 of CD44).

Six histidine residues (codons) were inserted in the N-terminal region of the HIV2 (gp32)-CD44 exon 6 fusion protein at the DNA level for the purpose of simpler antigen/immunogen isolation by means of metal chelate affinity chromatography.

Recombinant DNA Technique

Standard methods were used to manipulate the DNA such as those described by Sambrook, J. et al. (1989) In: Molecular cloning: A laboratory manual. Cold Spring Harbor Press, Cold Spring Harbor, N.Y. The molecular biological reagents were used according to the manufacturer's instructions.

Construction of HIV2 (gp32)-partial gene (plasmid pUC18_HIV2-gp32)

The coding section of the amino acid 48–162 of the HIV2-gp32 gene was synthesized by overlapping chemical gene synthesis and subsequently subcloned in the plasmid pUC18. Production and description of the plasmid pUC18__HIV2-gp32 are described in the European Patent Application 0 440 207.

Construction of the *E. coli* expression vector pDS56-6HIS-HIV2-gp32

In the following plasmid construction, a fusion gene was constructed which codes for the N-terminal of the amino acid sequence MRGSHHHHHHTDPEF (poly-His tail) and the selected HIV2-g[32 antigen.

For this purpose, the vector pQE-10 was digested with restriction endonucleases BamHI and HindIII, and the approx. 3.4-kbp-long BamHI/HindIII-pQE-10 vector fragment isolated by agarose gel electrophoresis. The pQE-10 vector [synonym: pDS56/RBSII, 6×His(-1)] is sourced from Diagen, Germany, and is described in Stuber, D. et al. (1990) Immunol. Methods IV: 121–152. In a second preparation, the plasmid pUC18__HIV2-gp32 was digested by the restriction endonucleases BamHI and HindIII, and the ca. 400-bp-long BamHI/HindIII-HIV2-gp32 fragment isolated and ligated into the approx. 3.4-bp-long BamHI/HindIII-pQE-10 vector fragment. The desired plasmid was identified by restriction mapping and designated pDS56-6HIS-HIV2-gp32.

Construction of *E. coli* expression vector pDS56-HIV2-CD44 exon 6

In the following plasmid construction, a fusion gene was constructed which codes N-terminal for the amino acid sequence MRGSHHHHHHTDPEF (poly-His tail), the selected HIV2-gp 32 antigen, and 2 copies of the CD44 exon 6 antigen.

Two copies of the CD44 exon 6 gene were produced by polymerase chain reaction (PCR) [Mullis, K. B. and Faloona, F. A. (1987) Methods Enzymol. 155: 335–350].

In a first PCR reaction, the CD44 exon 5–6 DNA sequence from base pair position 397–538 was amplified (see FIG. 9: DNA sequence of HIV2(gp32)-CD44 exon 6 fusion gene) and provided with suitable singular restriction endonuclease cleavage sites (BamHI and HaeIII). Subcloned CD44 cDNA (Exon 5–11) and the following primer pair were used for amplification:

```
                BamHI
Primer (1):  5'-a a a a a a CGATCCc c g g c t a c c a c t t t g a t g a g c a c t a g t g c t a c-3'
                           Pro Ala Thr Thr Leu Met Ser Thr Ser Ala ...
                           Exon 5                    Exon 6

HaeIII
Primer (2):  5'-a a a a a a GGCCGGa g c c a t t t g t g t t g t t g t g t g-3'
```

The approx. 160-bp-long PCR product was digested with BamHI and HaeIII and the approx. 150-bp-long BamHI/HaeIII-CD44 exon 6 fragment isolated by agarose gel electrophoresis.

In a second PCR reaction, the CD44 exon 5–6 DNA sequence of base pair position 539–672 (see FIG. 9: DNA sequence of HIV2(gp32)-CD44 exon 6 fusion gene) was amplified and provided with suitable singular restriction endonuclease cleavage sites (HaeIII and HindIII) using subcloned CD44 cDNA exon 5–11 as template DNA and the following primer pair:

```
                HaeIII
Primer (3):  5'-a a a a a a CCGGCCACCACTt t g a t g a g c a c t a g t g c t a c-3'
                           Pro Ala Thr Thr Leu Met Ser Thr Ser Ala ...
                           Exon 5                    Exon 6

HindIII
Primer (4):  5'-a a a a a a AAGCTTTTATCAa g c c a t t t g t g t t g t t g t g t g-3'
```

The approx. 150-bp-long PCR product was digested by HaeIII and HindIII and the approx. 140-bp-long BamHI/HaeIII-CD44 (Exon 6) fragment isolated by agarose gel electrophoresis.

Then the BamHI/HaeII-CD44 exon 6 fragment from the first PCR reaction and the HaeIII/HindIII-CD44 exon 6 from the 2nd PCR reaction were ligated by 3-fragment ligation into an approx. 3.8-bp-long BglII/HindIII-pDS56-6HIS-HIV2-gp32 vector fragment. The desired plasmid was identified by restriction mapping and the PCR-synthesised DNA regions checked by DNA sequencing (construction: pDS56-HIV2-CD44 exon 6).

Expression of the HIV2(gp32)-CD44 exon 6 antigen in *E. coli*

To express the HIV2(gp32)-CD44 exon 6 antigen in *E. coli*, the *E. coli* K12 strain RM82 (a methionine revertant of EX8654, Murry, N. E. et al. (1977) Mol. Gen. Genet. 150: 53–61) was transformed with the HIV2(gp32)-CD44 exon 6 expression plasmid pDS56-HIV2-CD44 exon 6 (resistance ampicillin) and the lacI repressor plasmid pUHA1 (resistance kanamycin). Production and description of the plasmid pUHA1 are described in Stuber, D. et al. (1990) Immunol. Methods IV: 121–152.

RM82/pUHA1/pDS56-HIV2-CD44 exon 6 cells were cultured in DYT medium (1% (w/v) yeast extract, 1% (w/v) Bacto Tryptone, Difco, and 0.5% NaCl) with 50 mg/l ampicillin and 50 mg/l kanamycin up to an optical density of 0.6–0.9 at 550 nm, and then induced with IPTG (1–5 mmol/l end concentration). After an induction phase of 4–8 h, the cells were harvested by centrifugation, washed with 10 mmol/l phosphate buffer, pH 6.8, and stored at −20° C. until further processing.

The cell pellet from 1 ml of culture medium (RM82/pUHA2/pDS56-HIV2-CD44 exon 6 cells) was re-suspended in 0.25 ml 10 mmol/l phosphate buffer, pH 6.8, and 1 mmol/l EDTA and the cells mechanically lysed by means of a French press. After centrifugation, ⅕ volumes of 5×SDS sample buffer: 50 mmol/l Tris-HCl, pH 6.8, 1% SDS, 1% mercaptoethanol, 10% glycerol, and 0.001% bromophenol blue) was added to the supernatant. The insoluble cell debris fraction was resuspended in 0.3 ml 1×SDS sample buffer with 6–8M urea. The samples were then incubated for 5 min at 95° C. and centrifuged. Thereafter, the proteins were separated by SDS-polyacrylamide gel electrophoresis (PAGE) (Laemmli, U. K. (1970) Nature 227: 680–685) and stained with Coomassie Brilliant Blue R dye.

The HIV(gp32)-CD44 exon 6 antigen (FIG. 10) synthesized in *E. coli* was homogeneous and found exclusively in the insoluble cell fraction. The expression level for the HIV2(gp32)-CD44 exon 6 antigen was 30–50% in relation to the *E. coli* total protein.

Preparation of HIV2(gp32)-CD44 exon 6 antigen from *E. coli*

Cell lysis and preparation of inclusion bodies (IB's).

20 g (wet weight) of RM82/pUHA1/pDS56-HIV2-CD44 exon 6 cells were re-suspended in 100 ml 0.1 mol/l Tris-HCl, pH 7.0, at 0° C. 30 mg lysozyme was added, and the mixture was incubated for 20 min at 0° C. The cells were then lysed completely by mechanical high pressure dispersion, and the DNA was digested in 30 min at 25° C. by addition of 2 mmol/l MgCl$_2$ and 1 mg DNAase (Boehringer Mannheim, Germany, Cat. No. 154709). Then 50 ml 60 mmol/l EDTA, 6% Triton X100 and 1.5 mmol/l NaCl, pH 7.0, were added to the digested solution and this mixture incubated for a further 30 min at 0° C. The insoluble components (cell debris and IB's) were then centrifuged down on a Sorvall centrifuge. The pellet was resuspended in 100 ml 0.1 mol/l phosphate buffer, pH 8.5, incubated for 30 min at 25° C., and the IB product isolated by centrifugation.

Purification of the HIV2(gp32)-CD44 exon 6 antigen using metal chelate chromatography The 2.5 g IB pellet (wet weight) was suspended in 25 ml 6 mol/l guanidine-HCl, 0.1 mol/l phosphate buffer, pH 8.5, by stirring for 2 h at 25° C. The insoluble components were separated off by centrifugation and the clear supernatant applied to an NTA column equilibrated with 6 mol/l guanidine-HCl , 0.1 mol/l phosphate buffer, pH 8.5 (column volume: 50 ml, NTA gel from the Diagen Company, Germany; Hochuli, E. et al. (1988). Bio/Technology 6: 1321–1325).

The column was then washed with about 5 column volumes of 8 mol/l urea, 10 mmol/l Tris-HCl, and 0.1 mmol/l phosphate buffer, pH 8.5. Subsequently, the HIV2 (gp32)-CD44 exon 6 antigen was eluted with 8 mol/l urea and 0.1 mol/l phosphate buffer, pH 4.0, and the HIV2(gp32)-CD44 exon 6 antigen-containing fractions pooled.

Expression and isolation of the HIV2 (gp32)-carrier antigen in E. coli

Analogous to the HIV2 (gp32)-CD44 exon 6 antigen the HIV2 (gp32) carrier antigen was produced by using the plasmid pDS56-6HIS-HIV2-gp32.

Biotinylation of HIV2 (gp32)-CD44 exon 6 antigen

Biotinylation was performed with biotinoyl-★-aminocapronic acid-N-hydroxy- succinimide (Bi-X-NHS) (Boehringer Mannheim, Germany Cat. No. 1003933) in the molar ratios 1:3, 1:6, and 1:10. The fusion protein HIV2 (gp32)-CD44 exon 6 present in a concentration of 7.1 mg/ml in 8M urea, 0.1M sodium phosphate buffer, 10 mM Tris, pH ca. 6, was diluted with dialysis buffer (0.1M sodium phosphate buffer, 0.5% SDS, 10 mM DTT, pH 8.5) to 2 mg/ml and dialyzed against the aforementioned dialysis buffer at room temperature and further diluted to 1 mg/ml. The appropriate quantity of Bi-X-NHS was added to the fusion protein, incubated for 2 h at room temperature, and than the reaction was stopped by addition of 1M lysine/HCl, pH 6.5, to 2 mM. After dialysis against 0.1M sodium phosphate buffer, 0.5% SDS, pH 6.0, the reagent HIV2 (gp32)-CD44 exon 6-Bi was stored at −20° C.

The peptide HIV2 (gp32) was biotinylated analogous.

REFERENCES

Hochuli, E.; W. Bannwarth; H. Dbeli; R. Genz; D. Stuber (1988). Genetic approach to facilitate purification of recombinant proteins with a noval metal chelate adsorbent. Bio/Technology 6: 1321–1325

Laemmli, U. K. (1970). Cleavage of structural proteins during the assembly of the head of bacteriophage T4. Nature 227: 680–685

Mullis, K. B.; F. A. Faloona (1987). Specific synthesis of DNA in vitro via a polymerase-catalyzed chain reaction. Methods Enzymol. 155: 355–350

Murray, N. E.; W. J. Brammar, K. Murray (1977). Lambdoid phages that simplify the recovery of in vitro recombinants. Mol. Gen. Genet. 150: 53–61.

Sambrook, J.; E. F. Fritsch, T. Maniatis (1989). Molecular cloning: A laboratory manual. Cold Spring Harbor Press, Cold Spring Harbor, N.Y.

Screaton, G. R.; M. Bell, D.G: Jackson, F. B: Cornelis, U. Gerth, J. I. Bell (1992). Genomic structure of DNA encoding the lymphocyte homing receptor CD44 reveals at least alternatively spliced exons. Proc.

Natl. Acad Sci. 89: 12160–12164

Stuber, D.; H. Matile, G. Garotta (1990). System for high level production in Escherichia coli and rapid application to epitope mapping, preparation of antibodies, and structure-function analysis. Inmunol. Methods IV: 121–152

Example 9

Immunization of mice

Immunization of mice was performed according to Cianfriglia et al. (1983). Hybridoma, Vol. 2, No. 4: 451–457. As immunogen synthetic peptides corresponding to amino acid 1–13, 9–23, 19–33, 29–43 and 1–43 coupled to a carrier protein (see example 7) as well as the HIV2 (gp32)-CD44 exon 6 antigen were used.

12-week old Balb/c mice were immunized with 50 μg immunogen in complete Freund's adjuvant intraperitoneally 15 and 8 days prior to fusion. 3 days before fusion, they were immunized intraperitoneally with 200 μg immunogen in PBS buffer, and 2 days before fusion and on the last day before infusion they were immunized both intraperitoneally and intravenously with 100 μg immunogen in PBS buffer.

Fusion and cloning

Manufacture of spleen cell suspension

Mice were terminated by cervical dislocation, and their spleens removed under sterile conditions. The spleen cells were teased out of the connective tissue in RPMI 1640 basic medium. The cell suspension was then passed through a sieve and centrifuged at 200 g (centrifuge tubes) in RPMI basic medium.

Fusion

Spleen cells from an immunized mouse were mixed in a ratio 1+5 with P3×63Ag8- 653 myeloma cells (ATCC CRL 8375) and centrifuged (10 min, 300 g, 4° C.). The cells were washed again with RPMI basic medium and centrifuged at 400 g . The supernatant was decanted off and then 1 ml PEG (Mr 4000,Merck) was added and mixed by pipetting. After 1 min on a water bath, 5 ml RPMI 1640 basic medium was added drop-wise at room temperature over a period of 5–6 min and the mixture made up to 50 ml with medium (RPMI 1640+10% FCS). Subsequently this was centrifuged for 10 min at 400 g, 4° C. The sedimented cells were added to RPMI 1640 medium +10% FCS and seeded in 96-well culture plates at $2.5\times10^4$ spleen cells per well in 200 μl selection medium (100 μM hypoxanthin, 1 μg/ml azaserin in RPMI 1640+10% FCS) [FCS=fetal calf serum].

After 10 days, these primary cultures were tested for specific antibody synthesis. Primary cultures of appropriate specificity were cloned in 96-well culture plates using an FACS (cell sorter). As growth factor, Interleukin 6 (Boehringer Mannheim Cat. No. 1271172, 100 U/ml) was added to the medium.

In this way, the following hybridoma cell lines were isolated; they have been deposited at the DMS facility in Braunschweig:

MAK<CD44>M-1.1.12

MAK<CD44>M-2.42.3

MAK<CD44>M-4.3.16

For MAK<CD44>M-1.1.12 a synthetic peptide corresponding to amino acids 9–23 , for MAK<CD44>M-2.42.3 a synthetic peptide corresponding to amino acids 29–43 and for MAK<CD44>M-4.3.16 a synthetic peptide corresponding to amino acids 1–13 of the CD44 exon 6 peptide having the amino acid sequence shown in FIG. 7 was used.

Antibody production

Obtaining antibodies from ascites $5\times10^6$ hybrid cells were injected i.p. into two mice pre-treated with 0.5 ml Pristan. After 1–3 weeks, ascites with an IgG concentration of 5–20 mg/ml was obtained. From this antibodies were isolated in the usual manner.

Obtaining antibodies from cell culture supernatants

Hybridoma cells were multiplied over a period of 7 days at an inoculation density of $1\times10^5$ cells/ml in RPMI 1640+ 10% FCS on a Techne biological stirrer (THERMO-DUX, Wertheim/Main, Model MCS-104XL, Cat. No. 144-050). Mean concentrations of 100 μg MAB/ml were achieved in the culture supernatant. Purification was performed using standard protein chemistry methods.

Example 10
Assessment of the specificity of the produced antibodies
Antibodies to synthetic CD44 peptide To establish antibody specificity in the hybridoma cell-culture supernatant, reactivity towards the partial peptide sequence and the entire exon 6 was determined in parallel by inhibition test. 96-well titer plates (Nunc) were coated with 200 μl/well of streptavidin [10 μg/ml, coating buffer=0.2 mol/l sodium carbonate/bicarbonate]. After coating with streptavidin, the biotinylated peptide e.g. 1–13 biotin, 9–23 biotin, 19–33 biotin, 29–43 biotin, c=2.5 μg/ml was bound in incubation buffer [sodium phosphate buffer, 40 mM, 0.5% Crotein C, 100 μl/well, incubation 1 h, room temperature]. The free binding sites were saturated with blocking buffer [0.9% NaCl, 1% Crotein C, 200 μl, 30 min, room temperature].

The antibody solution to be tested with and without the free peptide Exon 6 (1–43)NH$_2$, c=5 μg/ml was added and incubated for one hour. After a further wash step [0.9% NaCl, 0.05% Tween], 100 μl of a POD-labelled Fab fragment from sheep-sourced polyclonal antibody to mouse-kappa and mouse lambda [BM, mouse Ig determination kit, bottle 2 and bottle 6] was added. It was incubated for 1 h at room temperature. After a further wash step the color substrate, 100 μl, [ABTS, BM: #811769, #687359] was incubated for 30 min at room temperature, The absorbance at 450/490 nm was measured on a Dynatech MR 700 microplate reader.

All positive antibodies including the deposited cell lines were afterwards screened by dot-blot and immunohistology.
Antibodies to recombinant CD44 (fusion protein)

To determine antibody specificity from fusions with recombinant CD44 as antigen, additional screening tests were employed. Antibody samples were tested for reactivity with the fusion protein and for cross-reaction with HIV-gp32 in a parallel ELISA assay. The streptavidin-coated microtiter plates (see section 1) were incubated with biotinylated fusion protein HIV2(gp32)-CD44 exon 6-Bi(XOSU) or HIV2(gp32)-Bi(XOSU) [c=5 μg/ml, 100 μl/well, 1 h room temperature]. The free binding sites were blocked with blocking buffer [0.9% NaCl, 1% Crotein C, 200 μl, 30 min room temperature]. After a wash step [0.9% NaCl, 0.05% Tween] the antibody sample c=5–10 μg/ml, dilted in incubation buffer (40 mM sodium phosphate buffer], 100 μl per well and was incubated for 1 h at room temperature. The following steps were done as in the above examples for the synthetic peptide.

Some primary cultures with strong reactivity to the recombinant CD44 and low cross-reactivity towards HIV2 (gp32) protein were obtained. These cultures were further assessed by dot-blot and immunohistology.
Determination of specificity of antibodies to cells and tissue (immunostaining)

Method A: Cells from tumor cell lines (e.g. ZR-75 1 or MDA 4A4) were detached from the flask by scraping and the cell suspensions were dropped onto glass slides, dried and fixed with methanol.

Method B: Freeze-dried sections of tumor and normal tissue were fixed with acetone.

After blocking with 5% skimmed milk-TBS at 37° C. for 60 min, followed by washing with TBS for 2 min, the sample (undiluted cell-culture supernatant) was incubated with antibody for 120 min at 37° C. After carefully washing with TBS X3, further incubation was performed with biotinylated anti-mouse Ig (Dakopatts) for 60 min at 37° C. After further washing (TBS) HRPO avidin-biotin complex (Dakopatts) was added and incubated with the sample at room temperature for 60 min. After washing with TBS X1 1% glutaraldehyde solution was added for 1 min at room temperature. After a further wash step, the substrate (DAB) was added and incubated with the sample (15–20 min). After washing with tap water the nuclei were stained with hematoxylin for 30 sec. The samples were dried and embedded with Cristal Mount (Kaiser's jelly).

The results obtained with monoclonal antibody from cell lines MAB<CD44>M-1.1.12 and 4.3.16 are presented in Table 4. In Method B, the MAB 1.1.12 shows high specificity for tumor tissue from the lung, colon and bladder and MAB 4.3.16 revealed specificity for tumor tissue from the colon. In Method A, MAB 1.1.12 and MAB 4.3.16 showed increased reactivity to the cell line ZR-75-1 (exon 6 high-producer), a human breast cancer cell line (ATCC CRL 1500) than to the cell line MDA4A4 (exon 6 low-producer). This cell line is a subclone of cell line MDA-MB-435S (ductal carcinoma, breast, human; ATCC HTB 129; the subclone was produced according to Bao et al, Differentiation 52 (1993), 239–246;MDA4A4 is identical to MDA-MB-435-C2 of this reference).

Within the primary cultures obtained with the recombinantly produced CD44 fusion protein as immunogen (see above) the culture PK 9.00.22 showed a high specificity to tumor tissue of colon with method B. With method A this cultured cell line showed also a marked specificity for the cell line ZR 75–1.

TABLE 4

Results of Immunostaining

| | Method A cell suspension | | Method B tissue | |
|---|---|---|---|---|
| | ZR75-1 exon 6 high-producer | MDA4A4 exon 6 low-producer | tumor | normal |
| MAK 1.1.12 | + | − | lung | + | − |
| | | | colon | + | − |
| | | | bladder | + | − |
| MAK 4.3.16 | + | − | colon | + | − |

+ strong reaction;
− weak reaction

Determination of specificity of produced antibodies by dot-blot
Preparation of cell extracts Cells of lines HT29 (ATCC HTB 38—colon adenocarcinoma) and MDA4A4 were cultured in a medium according to ATCC catalogue and were harvested with or without protease additive.

The cells harvested without protease additive were centrifuged, added to double the volume of lysis buffer (50 mM potassium phosphate buffer, 150 mM NaCl, pH 8.0), homogenised for 5 min in a Dounce homogenizer and the quantity of protein determined. On the basis of this protein value, the cellular suspension was adjusted to a protein concentration of 1–2 mg/ml using lysis buffer with or without detergent [1% Triton X-100 (Boehringer Mannheim, Germany Cat. No. 743119), 0.6% CHAPS (Boehringer Mannheim, Germany Cat. No. 810681), 1% HECAMEG (Boehringer Mannheim, Germany Cat. No. 1382225), 0.9% octyl glucoside (Boehringer Mannheim, Germany Cat. No. 411469) or 0.05% dodecylmaltoside (Boehringer Mannheim, Germany Cat. No. 808342)] and stirred for 2 h. After the centrifugation, the supernatant which contains CD44 or CD44v was stored at 4° C. or −20°

C., and use unchanged. The supernatant obtained after centrifuging off the membranes contained sufficient CD44 (standard form) and CD44v (CD44 with additional exons) for antibody assessment. Because of the mRNA concentration in the cells, it is assumed that MDA4A4 contains predominantly CD44-standard form and hardly any exon 6-containing CD44v. HT29 cells, on the other hand, should contain mainly exon 6- containing CD44v.

A further simple way in which CD44 or CD44v can be obtained is to harvest the cells with trypsin instead of the aforementioned cell harvest with subsequent cellular separation. The supernatant obtained after addition of trypsin inhibitor and centrifuging off the cells also contains sufficient CD44 and CD44v for antibody assessment.

Assessment of antibodies by dot blot

Various solutions (synthetical produced CD44 exon6 peptide with the amino acid sequence 1–43 as shown in FIG. 7 according to example 7, HT29 cellular extract, MDA4A4 cellular extract) were applied to nitrocellulose by capillary tubes. After blocking with Crotein C, incubation of the nitrocellulose with the antibodies (AB) took place. As antibodies the supernatant of the various MAB<CD44>-M cell lines was used. Detection of bound Ab is done with a polyclonal anti Ig antibody conjugated to alcalic phosphatase. For color reaction NBT/X phosphate was used.

The specificity of the reaction can be shown by addition of free Exon6 peptide to the Ab before incubation of the nitrocellulose. If the reaction is specific for Exon6 or CD44v, either no or only very slight binding of the AB to the nitrocellulose takes place after addition of the free peptide. Best results were obtained with the following clones:

MAB<CD44>M-1.1.12

MAB<CD44>M-2.42.3

The following compounds were spotted onto the nitrocellulose (Schleicher & Schuell 401180) using capillary tubes:

A: synthetically produced CD44 exon 6, 1–43-NH$_2$, (0.1 mg/ml)

B: HT29 extract (1.2 mg/ml)

C: MDA4A4 extract (1.35 mg/ml)

After blocking the nitrocellulose with incubation buffer (20 mM Tris/HCl, 150 mM NaCl, 1% Crotein C, pH 7.4), in each case one blot with 2 or 3 dots was incubated using cell culture supernatant (in each case undiluted or diluted 1:4, 1:16, 1:64, 1:256 and 1:1024 in incubation buffer). The bound antibody was detected with PAB<M-Ig>S-Fab-AP and 5-bromo-4-chloro-3-indolyl-phosphate/4-nitroblue-tetrazolium chloride (NBT/X phosphate) as color substrate.

To test the AB specificity the test was run twice in parallel, performing pre-incubation of the antibody in one of the tests using 10 fg/ml of the free Exon6, 1–43 peptide. Inhibition should be seen for an exon 6-specific reaction.

The antibodies produced by the cell lines MAK<CD44>M-1.1.12 and MAK<CD44>M-2.42.3 are able to bind to dotted CD44 exon 6 peptide and to an extract of HT29 cells but not to an extract of MDA4A4 cells. Binding of the monoclonal antibody to dotted CD44 exon 6 peptide and to an extract of HT29 cells is specific for the tumorspecific variant of CD44v because preincubation of both antibodies with synthetic CD44 exon 6 inhibits the binding of the antibodies to nitrocellulose (Table 5).

TABLE 5

Results of dot-blots

| Dot-Blot results | Binding to extract of HT 29-cells | | Binding to extract of MDA4A4-cells | |
| --- | --- | --- | --- | --- |
| monoclonal antibody | no preincubation of mAb | preincubation of mAb with peptide exon 6 | no preincubation of mAb | preincubation of mAb with peptide exon 6 |
| MAK<CD44>M-1.1.12 | moderate | low (weak inhibition) | no | no |
| MAK<CD44>M-2.42.3 | strong | no (strong inhibition) | no | no |

We claim:

1. Antibody that specifically binds to the peptide corresponding to CD44 exon 6 having the amino acid sequence shown in FIG. 7 (SEQ ID NO:1), its allele variations and phosphorylation and glycosylation products.

2. Antibody according to claim 1 which is monoclonal or polyclonal.

3. Monoclonal antibody which specifically binds to the peptide corresponding to CD44 exon 6 having the amino acid sequence shown in FIG. 7 (SEQ ID NO:1) obtainable by the hybridoma cell lines MAK<CD44>M-1.1.12, MAK<CD44>M-2.42.3 or MAK<CD44>M-4.3.16, Accession Numbers DSM ACC2156, DSM ACC2157 or DSM ACC2158, respectively.

4. Monoclonal antibody according to claim 1 which recognize the same epitope as the monoclonal antibodies produced by the hybridoma cell lines MAK<CD44>M-1.1.12, MAK<CD44>M-2.42.3 or MAK<CD44>M-4.3.16, Accession Numbers DSM ACC2156, DSM ACC2157 or DSM ACC2158, respectively.

5. Method for the production of an antibody according to claim 1 comprising:

injecting a suitable laboratory animal with an effective amount of an antigenic compound comprising the peptide corresponding to CD44 exon 6 having the amino acid sequence shown in FIG. 7 (SEQ ID NO:1), or its allele variations, collecting serum from this animal, and isolating the specific antibody by immunoabsorbant techniques.

6. Method for the production of an antibody according to claim 1 comprising:

injecting a suitable laboratory animal with an effective amount of an antigenic compound comprising the peptide corresponding to CD44 exon 6 having the amino acid sequence shown in FIG. 7 (SEQ ID NO:1), or its allele variations, isolating the antibody producing cells, immobilizing these cells, screening for the immortal cell line producing the antibody according to claim 1, cloning said immortal said cell line, and obtaining the antibody from ascites or the supernatant of the cultured immortal cell line.

7. Method for the production of an antibody according to claim 5, wherein as immunogen a fusion protein comprising the peptide corresponding to CD44 exon 6 having the amino acid shown in FIG. 7 (SEQ ID NO:1), or its allele variations or a peptide of at least six amino acid length corresponding to an amino acid sequence of CD44 exon 6 shown in FIG. 7, or its allele variations which is coupled to a suitable immunogenic carrier is used.

8. Immunoassay for the detection of a CD44 protein contained in the peptide corresponding to CD44 exon 6 wherein an antibody that specifically binds to the peptide CD44 exon 6 having the amino acid sequence shown in FIG. 7 (SEQ ID NO:1), or its allele variations is used.

9. Test kit comprising at least one antibody according to claim 2.

10. Monoclonal antibody according to claim 1, which is an antigen-binding fragment, or a humanized or human antibody.

11. Monoclonal antibody according to claim 10, which is a human IgG1 antibody.

12. Immunoassay according to claim 8 for cancer diagnosis.

13. Immunoassay according to claim 8, for the detection of a complex of the antigen with a second antibody.

* * * * *